(12) United States Patent
Ozawa

(10) Patent No.: US 11,054,304 B2
(45) Date of Patent: Jul. 6, 2021

(54) IMAGING DEVICE AND METHOD

(71) Applicant: Sony Corporation, Tokyo (JP)

(72) Inventor: Ken Ozawa, Kanagawa (JP)

(73) Assignee: Sony Corporation, Tokyo (JP)

( * ) Notice: Subject to any disclaimer, the term of this patent is extended or adjusted under 35 U.S.C. 154(b) by 365 days.

(21) Appl. No.: 15/313,173

(22) PCT Filed: Jun. 17, 2015

(86) PCT No.: PCT/JP2015/003023
§ 371 (c)(1),
(2) Date: Nov. 22, 2016

(87) PCT Pub. No.: WO2015/198562
PCT Pub. Date: Dec. 30, 2015

(65) Prior Publication Data
US 2017/0184449 A1    Jun. 29, 2017

(30) Foreign Application Priority Data

Jun. 26, 2014 (JP) .............................. JP2014-131808

(51) Int. Cl.
*H01L 27/00* (2006.01)
*G01J 1/42* (2006.01)
(Continued)

(52) U.S. Cl.
CPC .............. *G01J 1/42* (2013.01); *A61B 5/0075* (2013.01); *A61B 5/14551* (2013.01);
(Continued)

(58) Field of Classification Search
CPC ...... G01J 3/0205; G01J 3/2823; G01J 3/4531; G01J 3/0208; G01J 3/0224; G01J 3/027;
(Continued)

(56) References Cited

U.S. PATENT DOCUMENTS 5,386,431 A * 1/1995 Tulip .................... H01S 3/0315
359/346
2003/0016901 A1    1/2003 Cormack
(Continued)

FOREIGN PATENT DOCUMENTS

JP       2008-309706 A    12/2008
WO    WO-2006018897 A1 *  2/2006 ................ G01J 9/02
(Continued)

OTHER PUBLICATIONS

Kudenov et al., "Compact snapshot birefringent imaging Fourier transform spectrometer", Proceedings of SPIE, vol. 7812, Aug. 12, 2010, DOI: 10.1117/12.864703.
(Continued)

*Primary Examiner* — Georgia Y Epps
*Assistant Examiner* — Kevin Wyatt
(74) *Attorney, Agent, or Firm* — Wolf, Greenfield & Sacks, P.C.

(57) ABSTRACT

An imaging device and method are provided. Light from an object is provided as a plurality of sets of light beams to a phase difference array having a plurality of elements. The phase difference array is configured to provide different optical paths for light included within at least some of a plurality of sets of light beams. The light from the phase difference array is received at an imaging element array. The imaging element array includes a plurality of imaging elements. Information obtained from hyperspectral imaging data based on output signals of the imaging element array can be displayed.

24 Claims, 16 Drawing Sheets

(51) Int. Cl.
*G01J 3/28* (2006.01)
*G01J 4/04* (2006.01)
*G01J 3/02* (2006.01)
*G01J 3/453* (2006.01)
*A61B 5/1455* (2006.01)
*G01N 21/31* (2006.01)
*A61B 5/00* (2006.01)
*G01N 21/359* (2014.01)
*G01J 1/04* (2006.01)
*G01N 21/35* (2014.01)
*G01J 4/00* (2006.01)
*A61B 5/145* (2006.01)

(52) U.S. Cl.
CPC .......... *A61B 5/14558* (2013.01); *A61B 5/681* (2013.01); *G01J 1/0411* (2013.01); *G01J 1/0429* (2013.01); *G01J 1/0488* (2013.01); *G01J 3/0205* (2013.01); *G01J 3/027* (2013.01); *G01J 3/0208* (2013.01); *G01J 3/0224* (2013.01); *G01J 3/2823* (2013.01); *G01J 3/4531* (2013.01); *G01J 4/04* (2013.01); *G01N 21/314* (2013.01); *G01N 21/359* (2013.01); *A61B 5/14532* (2013.01); *A61B 5/14546* (2013.01); *A61B 5/14552* (2013.01); *G01J 2004/005* (2013.01); *G01N 2021/3595* (2013.01)

(58) Field of Classification Search
CPC .......... G01J 4/04; G01J 1/0411; G01J 1/0429; G01J 1/0488; G01J 1/42
USPC ...................................... 250/208.1
See application file for complete search history.

(56) References Cited

U.S. PATENT DOCUMENTS

| | | | | |
|---|---|---|---|---|
| 2006/0066857 | A1* | 3/2006 | Ok | G01N 21/645 356/417 |
| 2006/0279741 | A1* | 12/2006 | Hirata | G01J 3/453 356/491 |
| 2013/0208284 | A1* | 8/2013 | Pouet | G01H 9/006 356/502 |
| 2015/0157261 | A1 | 6/2015 | Sakagami | |
| 2015/0281538 | A1* | 10/2015 | Boettiger | H04N 5/247 348/218.1 |

FOREIGN PATENT DOCUMENTS

WO WO 2014/002388 A1 1/2014
WO WO-2015198562 A2 * 12/2015 ............ G01J 3/0205

OTHER PUBLICATIONS

Meng et al., "Fourier transform imaging spectropolarimeter using simultaneous polarization modulation" Optics Letters, Optical Society of America, vol. 38., No. 5, Mar. 1, 2013, pp. 778-780, DOI: 10.1364/OL.38.000778.

Tyo et al., "Review of passive imaging polarimetry for remote sensing applications" Applied Optics, Optical Society of America, vol. 45, No. 22, Aug. 1, 2006, pp. 5453-5469, DOI: 10.1364/AO.45.005453.

International Search Report and Written opinion dated Feb. 2, 2016 in connection with International Application No. PCT/JP2015/003023.

International Preliminary Report on Patentability dated Jan. 5, 2017 in connection with International Application No. PCT/JP2015/003023.

* cited by examiner

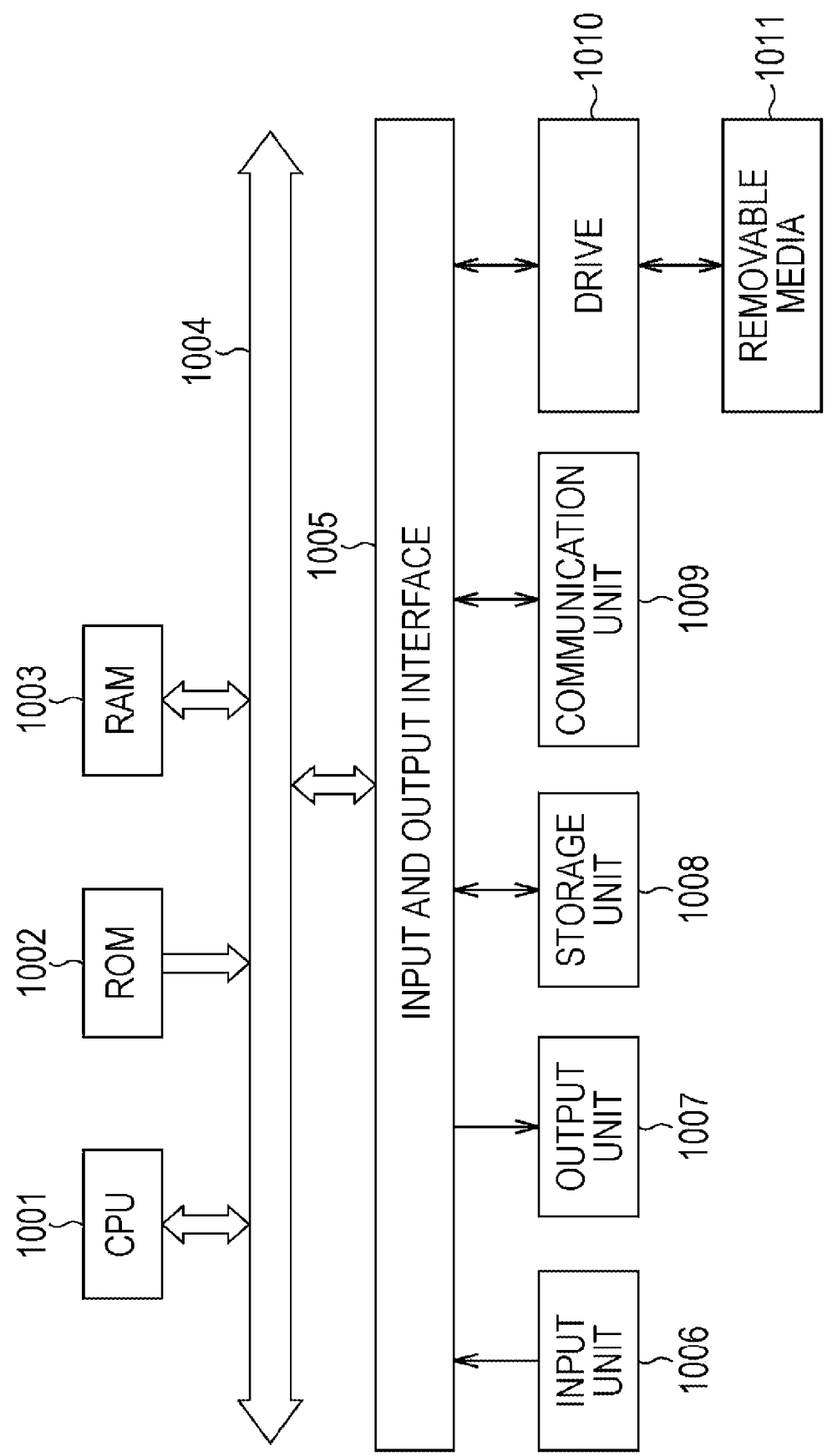

IMAGING DEVICE AND METHOD

CROSS REFERENCE TO RELATED APPLICATIONS

This application claims the benefit under 35 U.S.C. § 371 as a U.S. National Stage Entry of International Application No. PCT/JP2015/003023, filed in the Japanese Patent Office as a Receiving Office on Jun. 17, 2015, which claims priority to Japanese Patent Application JP 2014-131808, filed in the Japanese Patent Office on Jun. 26, 2014, the entire contents of each of which is incorporated by reference in its entirety.

TECHNICAL FIELD

The present technology relates to an imaging device and method, and in particular, relates to an imaging device and method capable of implementing hyper spectral imaging (HSI) of high sensitivity, without moving units.

CROSS REFERENCE TO RELATED APPLICATIONS

This application claims the benefit of Japanese Priority Patent Application JP 2014-131808 filed Jun. 26, 2014, the entire contents of which are incorporated herein by reference.

BACKGROUND ART

In recent years, in particular, hyperspectral imaging (hereinafter, simply also referred to as HSI) has attracted attention in which a continuous piece of spectral information for each pixel is obtained, among the multi-band imaging having an increased number of spectral bands, in addition to the three primary colors of red, green, and blue (RGB) which are handled by an imaging device such as a normal camera.

It is possible to obtain the spectral information of a narrow band on a pixel basis from a captured image by the HSI, therefore it is possible to spectrally analyze respective areas within one image, and to realize visualization of the specification, alteration, and state change of an object, and the like. Examples of the application field of HSI include healthcare, environment, food sanitation, agriculture, military and the like.

As a first method of the HSI in the past, it has been proposed that light from an object is cut by the slit, dispersed by a dispersive element referred to as a prism or a grating in a direction perpendicular to the longitudinal direction of the slit, and recorded by an imaging element such as an image sensor including a charge coupled device (CCD) and a complementary metal oxide semiconductor (CMOS) so as to scan the slit.

As a second method of the HSI in the past, it has been proposed that light from a light source is dispersed by an acousto-optic tunable filter (AOTF) so as to illuminate an object and scan a wavelength, therefore it is possible to sequentially acquire the reflected image of each wavelength.

Further, as a third method of the HSI in the past, it has been proposed that Fabry-Perot mirrors that are spaced differently for respective pixels are formed immediately above the imaging element, and thus the interval for performing dispersion of a narrowband by the respective Fabry-Perot mirrors is formed so as to be accurately controlled (see NPL 1).

Further, as a fourth method of the HSI in the past, it has been proposed that a phase modulation mirror is formed in a half area of a pupil plane of an afocal objective lens, and an interferogram obtained by shift-scanning the mirror is subjected to Fourier transform so as to obtain a spectroscopic spectrum of each image point (see PTL 1).

Further, as a fifth method of the HSI in the past, it has been proposed to spatially perform the temporal phase modulation in the fourth method (see NPL 2).

In other words, in the fifth method, a compound eye image is formed by a micro lens array (MLA), a prism (Nomarski Prizm) made of a birefringent material is placed on the image plane, and an optical path difference between a P-polarized light component and an S-polarized light component is controlled depending on the thickness of the prism such that light is re-imaged and recorded in the imaging element.

Interference images having different phase differences are recorded in respective MLAs (unit eye image), and an interferogram is obtained for each image point in the unit eye image (an output value at the same point of each unit eye image versus an added phase difference), and is subjected to Fourier transform, therefore it is possible to obtain a spectroscopic spectrum of each image point, in other words, an HSI data cube.

CITATION LIST

Patent Literature

PTL 1: Japanese Patent No. 5078004

Non Patent Literature

NPL 1: SPIE Vol. 8613, 861314-1, A Snapshot Multispectral Imager with Integrated, Tiled Filters and Optical Duplication, B. Geelen, et. al NPL 2: 2012/Vol. 20, No. 16/OPTICS EXPRESS 17985, Compact real-time birefringent imaging spectrometer, M. W. Kudenov, et. al

SUMMARY OF INVENTION

Technical Problem

The HSI can be realized with a relatively simple structure by using the first method described above, however, a driving unit itself referred to as the slit scan would be a cause of failure. It is difficult to implement the HSI of a moving image due to the slit scan. Further, since energy is dispersed for each wavelength by the dispersion element, the energy input to one pixel of the imaging element becomes weak, and the sensitivity of the system is low, such that a broadband light source having a large output is necessary. Further, the spatial resolutions in the scanning direction are averaged by the width of the slit, and this limits a rate.

Further, the HSI can be realized with a relatively simple structure by using the second method, and the wavelength scanning is electrically driven by the AOTF, such that mechanical moving units are not present, but since it involves wavelength scanning, it is difficult to implement the HSI of a moving image. Further, since the spectral image for each wavelength is captured at a different time, it is difficult to ensure the simultaneity of the spectral images. In addition, since the light source of broadband wavelength is spectrally extracted by the AOTF, power per one spectral wavelength is weak and thus system sensitivity is low.

The HSIs of the first and second methods in the past have already been commercialized as spectrometers, but the entire system size including even a lighting device becomes large, therefore portability is not good, and it is expensive.

Further, since the components necessary for the HSI of the third method are formed in a semiconductor process, there is an advantage such as miniaturization of the device and cost reduction. However, since the Fabry-Perot mirror is a reflective type narrow-band spectral filter system, as the wavelength resolution is increased, that is, the dispersion of a narrow band is performed, the light utilization efficiency is low and thus the broadband light source needs to have a large output, such that as a whole, it is difficult to achieve miniaturization.

In the fourth method, there are examples in which the light utilization efficiency is high and a method other than a filter method is used. Therefore, first, energy loss is low and efficiency is high because of using an interference image, and thus a light source having a high output is not necessary. Second, a configuration to simultaneously obtain the spectral images of respective wavelengths which are finally obtained is ensured in principle. Third, it is possible to easily reduce the wavelength resolution by making a shift range of the mirror large. Fourth, since it is not necessary to use special materials, the configuration can be made at a low cost.

However, in the fourth method, since the shift of mirror is necessary, it is difficult to obtain a moving image.

Further, in the fifth method, similar to the fourth method described above, first, energy loss is low and efficiency is high because of using an interference image, and thus the light source having a high output is not necessary. Further, second, a configuration to simultaneously obtain spectral images of the respective wavelengths which are finally obtained is ensured in principle. Since the moving unit is not present, there is an advantage that there is not a portion that becomes a cause of failure.

However, the phase difference is formed using a prism made of a birefringent material, and the material is special, and thus applying a prism shaping process with the special materials to the semiconductor process is difficult. As a result, cost is increased.

In other words, the fourth and fifth methods allow obtaining of the HSI data cube by performing a Fourier transform on the interference image, and conforming to an FT-IR device (Fourier transform infrared spectrophotometer), which is widely used in the component analysis of an organic material in principle, and thus there are well-made algorithms which are reliable.

However, in the fifth method, since it is necessary to use a special material referred to as a birefringence material, cost is increased.

The present technology has been made in view of such circumstances. According to embodiments of the present disclosure, a method of extracting a spectral image is achieved by performing a Fourier transform on an interference image without using a filter, in particular, with a structure that does not require moving units or special materials, and that can employ a semiconductor process capable of being implemented at relatively low cost.

Solution to Problem

According to an embodiment of the present disclosure, there is provided an imaging device that includes a phase difference array with a plurality of elements, wherein the phase difference array is configured to provide different optical paths for light included within at least some of a plurality of sets of light beams, and an imaging element array including a plurality of imaging elements, wherein at least one of the imaging elements is configured to receive one of the sets of light beams from the phase difference array.

According to other embodiments of the present disclosure, there is provided a detection apparatus that includes a connecting structure, a light source, and an enclosure. The light source and the enclosure are connected to the connecting structure. The enclosure includes a phase difference array with a plurality of elements, wherein the phase difference array is configured to provide different optical paths for light included within at least some of a plurality of sets of light beams. The enclosure also includes an imaging element array including a plurality of imaging elements, wherein at least one of the imaging elements is configured to receive one of the sets of light beams from the phase difference array. In addition, the detection apparatus includes a display, wherein the display is connected to the connecting structure, and wherein the display is operable to display detection information generated from data provided by the imaging element array.

According to yet other embodiment of the present disclosure, there is provided a method for detecting a physical property that includes emitting light onto an object, receiving light from the object at a plurality of phase difference elements included in a phase difference array, wherein at least some of the phase difference elements generate a phase difference from the light incident on the phase difference elements, receiving light from the phase difference elements at an imaging element array, and displaying information obtained from hyperspectral imaging (HIS) data based on output signals of the imaging element array.

According to an embodiment of the present technology, the same imaging area is captured as a plurality of unit images by the imaging element array, and respective different optical path differences are caused by the phase difference array in a portion of the respective imaging areas of the plurality of unit images which are captured by the imaging element array.

The imaging device according to an embodiment of the present technology may be an independent apparatus, or may be a block that performs an imaging process.

Advantageous Effects of Invention

According to an embodiment of the present technology, it is possible to capture an HSI image of high sensitivity.

BRIEF DESCRIPTION OF DRAWINGS

FIG. 16 is a diagram illustrating a configuration example of a general-purpose personal computer.

DESCRIPTION OF EMBODIMENTS

Figure 1:
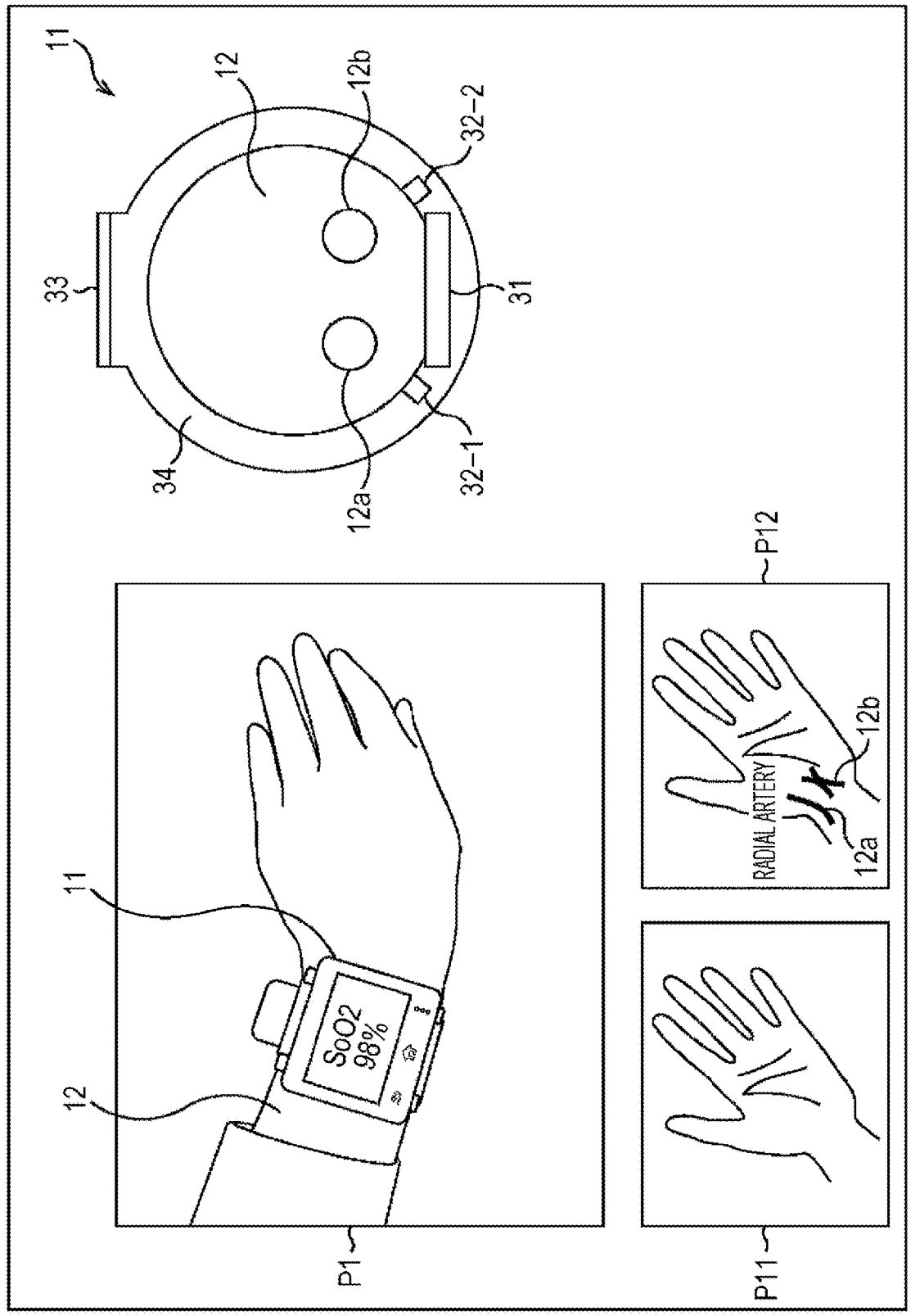
FIG. 1 is a diagram illustrating a configuration example of an embodiment of a blood test apparatus employing an imaging device of the present technology.

Example of Applying Imaging Device of the Present Technology to Blood Test Apparatus FIG. 1 illustrates a configuration example of an embodiment of a blood test apparatus employing an imaging device of the present technology. The blood test apparatus 11 of FIG. 1 analyzes blood components in a blood vessel, based on a hyper spectral imaging (HSI), which is captured by a built-in imaging device, and measures and displays blood information such as an oxygen concentration, a lipid level, and a blood glucose level in blood.

More specifically, for example, as illustrated in an external view P1 in the upper left part in FIG. 1, the blood test apparatus 11 is used while being worn like a watch along the arm 12 of a person who is the user so as to capture images of an artery 12a and a vein 12b inside the arm 12, and detect components contained in the blood from spectral reflectance data of the artery 12a and the vein 12b which are captured as the HSI 31.

As illustrated in the upper right part of FIG. 1, the blood test apparatus 11 includes, for example, a body 31, light sources 32-1 and 32-2, a display unit 33, and a connecting structure, for example in the form of a strap or belt 34. The blood test apparatus 11 has a configuration in which the body 31, the broadband light sources 32-1 and 32-2 such as halogen including a near-infrared light component, and the display unit 33 are provided on the belt 34 and are respectively electrically connected. The blood test apparatus 11 is secured to the arm 12 by being worn around the arm 12. Further, the upper right part of FIG. 1 is a vertical cross-sectional view along an axis, with the longitudinal direction of the bone constituting the arm 12 with the axis, in a state where the blood test apparatus 11 is secured to the arm 12 by being worn around the arm 12 by using the belt 34.

The HSI body 31 includes an imaging device that captures the HSI, is provided facing the arm 12 in a state where the blood test apparatus 11 is worn around the arm 12 by the belt 34, and captures a reflected image caused by the light emitted from the light sources 32-1 and 32-2 being reflected on the blood (artery blood) inside the artery 12a and the blood (vein blood) inside the vein 12b, inside the arm 12.

In this case, the body 31 captures an image in which the artery 12a and the vein 12b are projected by, for example, light of a red wavelength to near-infrared light, in an image at a few millimeters under a skin, as illustrated in an image P12 in the lower left part of FIG. 1, corresponding to the image of arm 12 that is visible to the human eye by visible light as illustrated by the image P11 in the lower left part of FIG. 1. As an example, the artery 12a is assumed to be radial artery. Since the visibility of the artery 12a is not significantly good, the artery 12a may be located by extracting beating portions from a moving image.

Further, the body 31 spectrally analyzes the blood in the captured artery 12a and the vein 12b, measures the oxygen concentration, the lipid level, and the blood glucose level in the blood, and displays the measurement result and information corresponding to the measurement result, on the display unit 33.

Configuration Example of Body

Next, the configuration of the body 31 will be described with reference to the block diagram of FIG. 2. The body 31 includes a camera array 51 and a signal processing unit 52.

The camera array 51 is configured with a plurality of, for example, m×n camera units that are arranged in the vertical direction and the horizontal direction. The same imaging area is cut and subjected to parallax correction such as an XY shift. The plurality of camera units capture interference images in which respective different wavelengths are emphasized, and output the interference images to the signal processing unit 52.

Figure 2:
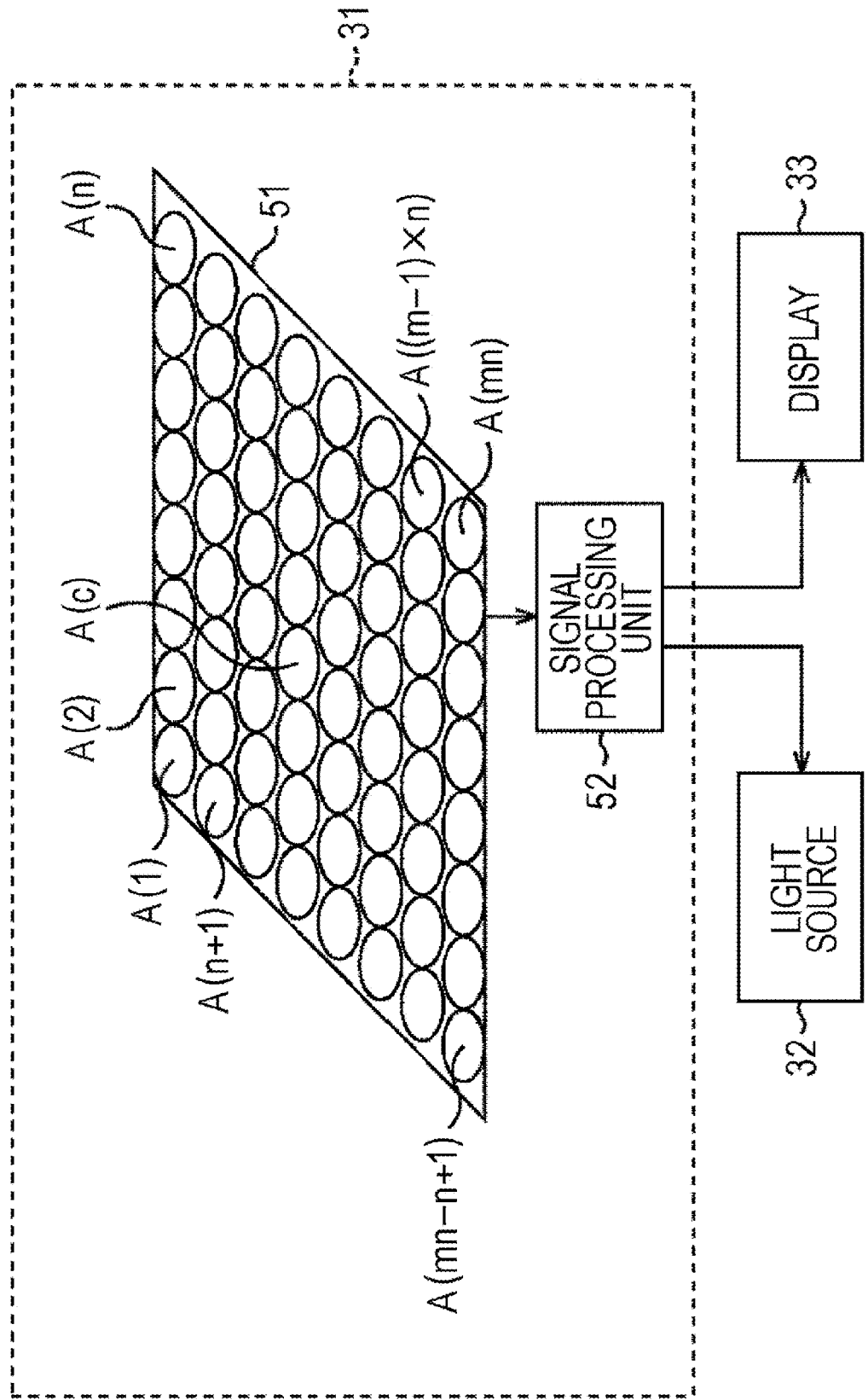
FIG. 2 is a block diagram illustrating a configuration of the blood test apparatus.

Further, FIG. 2 illustrates an example in which n camera units are arranged in the horizontal direction and m camera units are arranged in the vertical direction, in the camera array 51. Further, camera units A(1), A(2), A(3), . . . A(n-1), and A(n) are sequentially arranged from the left to the right, respectively at a top row in the horizontal direction in FIG. 2. Further, even in the second row from the top, from the left to the right, camera units A(n+1), A(n+2), and A(n+3) are sequentially arranged. Then, even in the bottom row, from the left to the right, camera units A(mn-n+1), A(mn-n+2), and A(mn-n+3) are sequentially arranged, and a camera unit A(mn) is arranged in the rightmost column at the bottom row. In the following description, if respective camera units on the arrangement are distinguished, the camera units are referred to as the camera units A(mn) described above, however, if the camera units are not distinguished, they are simply referred to as a camera unit A.

The signal processing unit 52 generates an interferogram by reading image signals which are supplied from respective camera units A and includes interference images in which different wavelengths are emphasized, in units of pixels at the same position. Further, the signal processing unit 52 generates data configured with spectroscopic spectra, by performing a Fourier transform on the interferogram in units of pixels. Then, the signal processing unit 52 analyzes the necessary components such as the oxygen concentration, the lipid level, and the blood glucose level in the blood based on the generated data configured with spectroscopic spectra, and displays the analysis result on the display unit 33. Here, during imaging, the signal processing unit 52 causes the light sources 32-1 and 32-2 to emit light. Further, in the following description, if the light sources 32-1 and 32-2 are distinguished, they are simply referred to as the light source 32, and other components are assumed to be referred to in the same manner.

DETAILED CONFIGURATION OF CAMERA ARRAY

Figure 3:
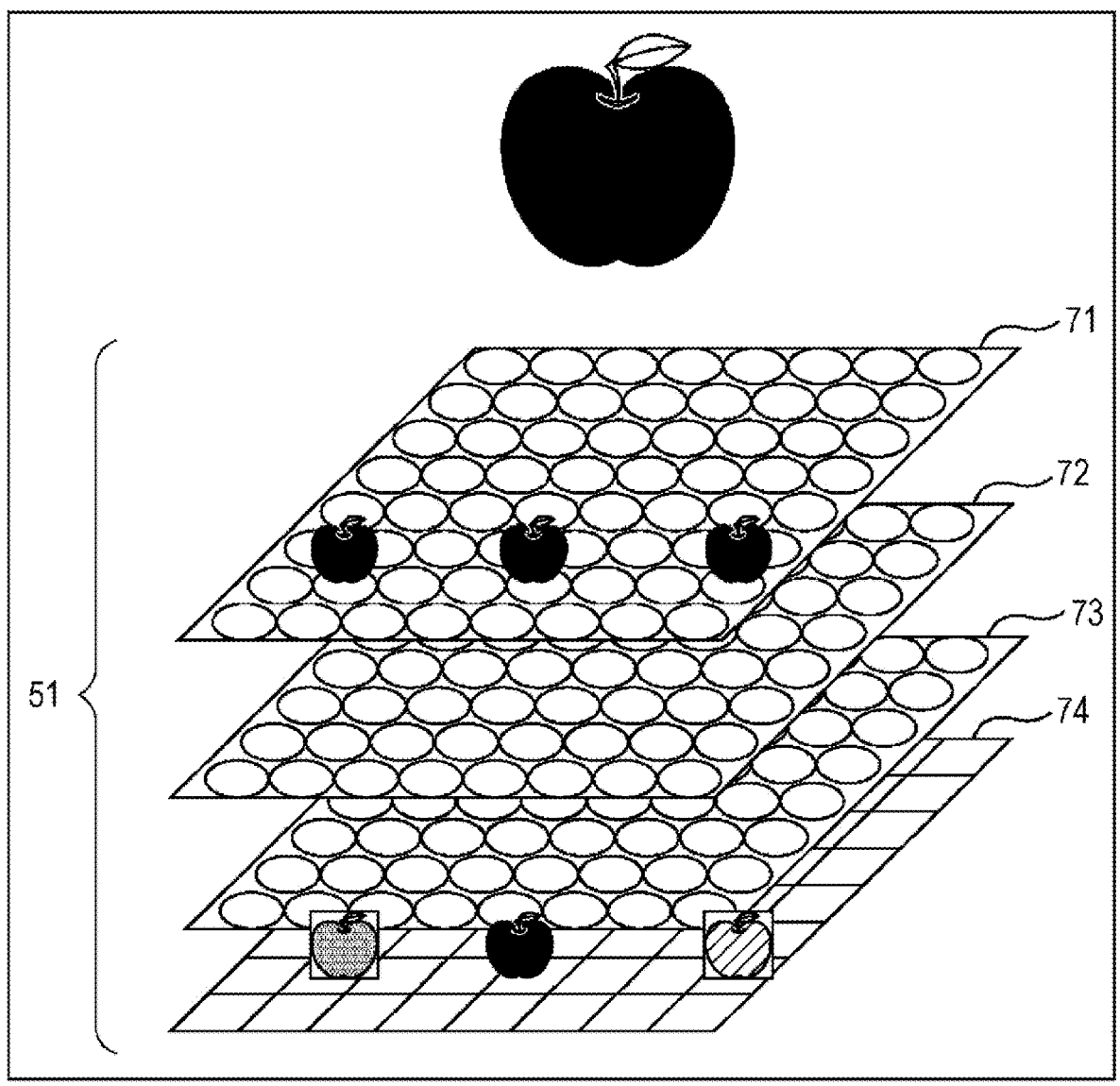
FIG. 3 is a diagram illustrating a configuration of a camera array.

Next, the configuration of the camera array 51 will be described in detail with reference to FIG. 3.

The camera array 51 is configured with a lens array 71, a phase difference array 72, and a lens array 73, which are optical elements, and an imaging element array 74. Further, an apple image in FIG. 3 indicates an object. In other words, the light from the object propagates, in the order of the lens array 71, the phase difference array 72, the lens array 73, and the imaging element array 74.

The lens array 71 is, for example, an array of objective lenses which are configured for the respective camera units of a focal length f, and the lens array 71 converts the incident light into cylindrical parallel light beams with respect to the respective camera units A, and inputs the parallel light beams to the phase difference array 72. In particular, an objective lens is provided for each camera unit A of the imaging element array, and each of the objective lenses creates a set of parallel light beams from the incident light for its respective camera unit A.

The phase difference array 72 includes a plurality of phase difference elements that are defined by light shielding portions 72a. For example, one phase difference element can be provided for each set of parallel light beams formed by the lens array 71. At least some of the elements of the phase difference array 72 include a filter that covers a portion of the parallel light beams incident from the lens array 71 with an object 72b having a predetermined refractive index. The elements of the phase difference array 72 associated with such an object 72b generate an optical path difference between the light beams passing through an area of the element covered with the object 72b and the light beams passing through an area of the element not converted with the object. The phase difference array 72 generates a phase difference corresponding to the optical path difference, and inputs the phase difference to the lens array 73 as an imaging lens array. In particular, the phase difference array 72 can include an element for or corresponding to each camera unit A. The phase differences are different for respective camera units A, and the phase difference may be zero in some cases. In addition, in FIG. 2, the camera unit A of which the phase difference becomes zero is referred to as, in particular, a camera unit A(C) in FIG. 2.

The lens array 73 is an array of imaging lenses, and images the light flux with the phase difference added by the phase difference array 72, on the imaging element array 74, in units of the camera units A. In other words, the interference image is obtained.

The imaging element array 74 is configured with complementary metal oxide semiconductor (CMOS) image sensors, captures different interference images in units of the camera units A, and outputs image signals of the captured interference images to the signal processing unit 52. In other words, the imaging element array 74 is a single imaging element as a whole, and the camera units A described above are obtained by classifying the pixels on the imaging element, for each imaging element area for capturing a unit image for capturing the same imaging area. Here, when obtaining the same imaging area, images are cut out for parallax correction, and subjected to an XY shift. Thus, the camera units A are not separate imaging elements, and a single imaging element area as a whole represents an area which is divided for each area of the predetermined number of pixels. That is, each of the camera units A includes a plurality of pixels. In addition, a monochrome imaging device without a color filter is used as the imaging element array 74.

Figure 4:
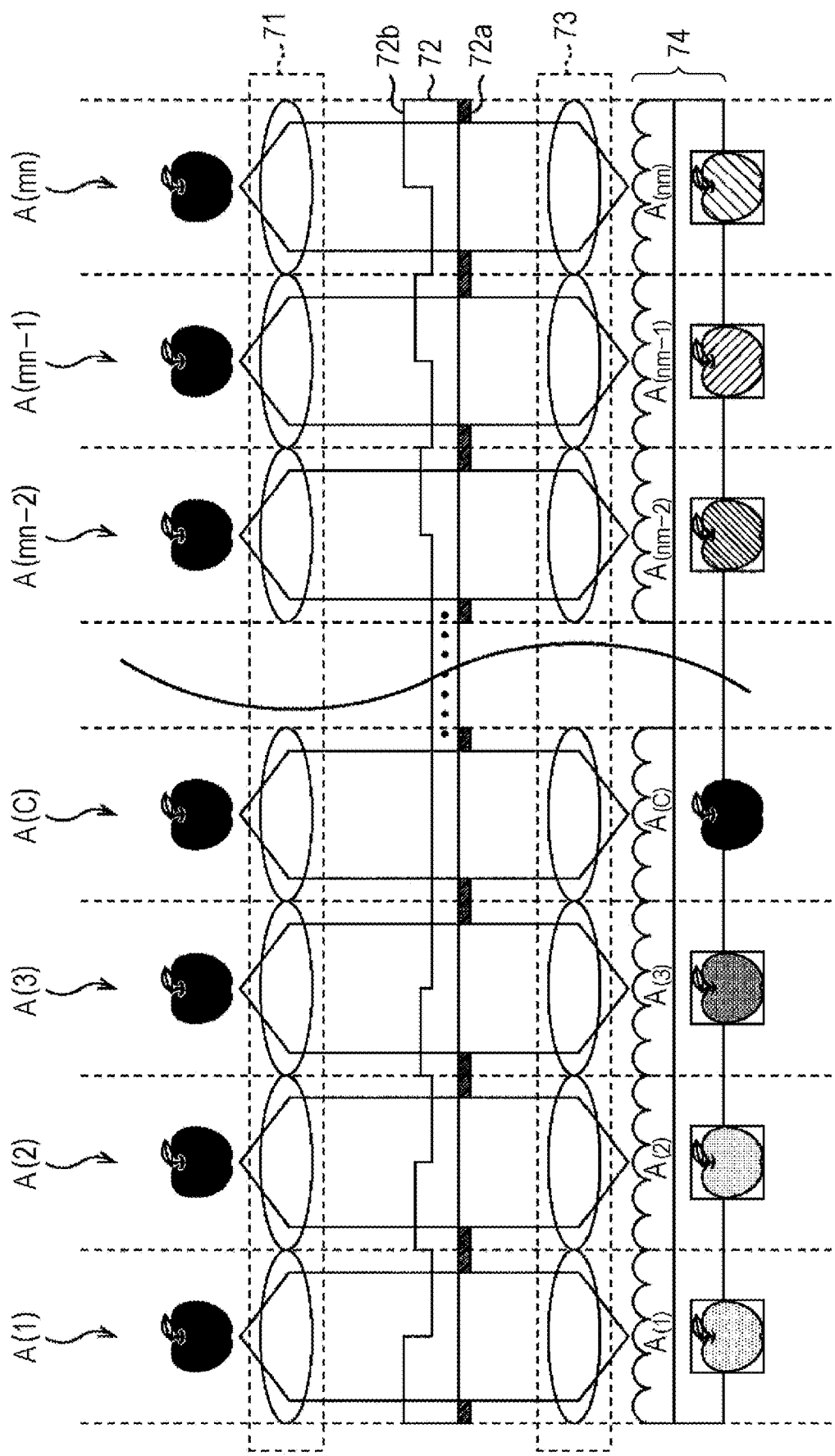
FIG. 4 is a diagram illustrating a configuration of the camera array.

In other words, as illustrated in FIG. 4, the lens array 71 as the objective lens array converts the incident light into parallel light beams of a range corresponding to respective camera units A(1) to A(mn). The phase difference array 72 causes a phase difference in the left and right parts of FIG. 4 by generating an optical path difference between some areas and the other areas of the parallel light beams by a filter-like object 72b of a predetermined refractive index, and inputs the light flux to the lens array 73 as the imaging lens array, by limiting the light flux by light shielding portions 72a configured with circular openings.

The lens array 73 as the imaging lens array images the light flux added with the phase difference on the imaging element array 74, in units of the camera units A, and causes the imaging elements constituting the imaging element array 74 to capture interference images in which different wavelengths are emphasized corresponding to the added phase difference, in units of the camera units A.

Figure 5:
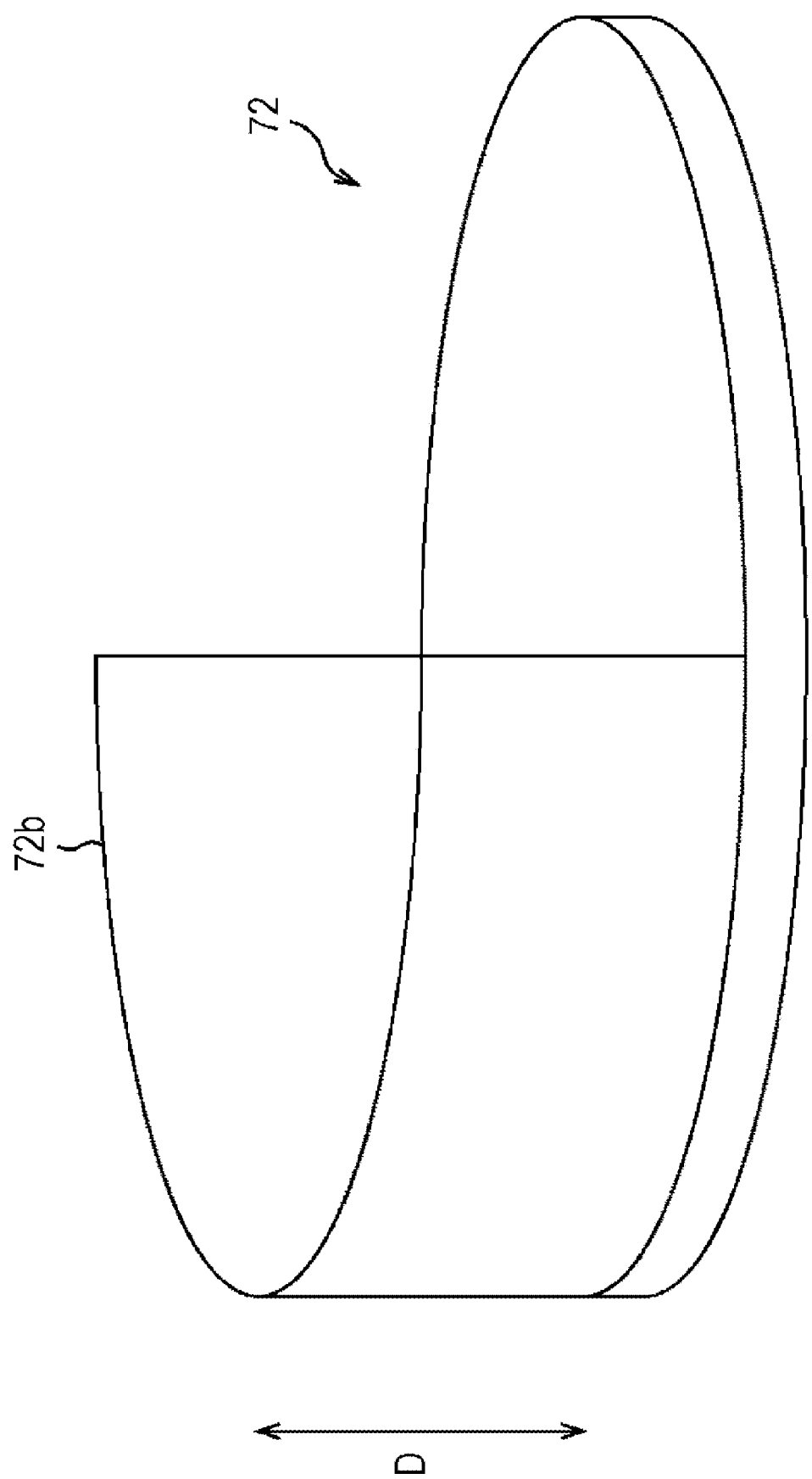
FIG. 5 is a diagram illustrating a configuration of a phase difference array.

Here, for example, as illustrated in FIG. 5, the objects 72b cause optical path differences corresponding to the thickness D of the object 72b, between the light in an area of an element covered with the object 72b and the light in the area of the element not covered with the object 72b, by covering a semicircular area with the object 72b, so as to generate interference images corresponding to the optical path differences. Further, as illustrated in FIG. 5, the interference images in which different wavelengths are emphasized are formed, by changing the thickness d of the object 72b with respect to the thickness of the remainder of the object 72.

In other words, for example, as illustrated in FIG. 4, when the camera units A(1), A(2), . . . A(mn) are provided, the thickness D of the object 72b in the left part of FIG. 4 is set to maximum, the thickness D becomes sequentially reduced, the thickness D is set to 0 (optical path difference=0) in the camera unit A(C) at the center position, and after this, in turn, the thickness D of the object 72b goes to be sequentially increased towards the right part of FIG. 4 at predetermined intervals, and the thickness D of the object 72b is adjusted to become maximized in the right part of FIG. 4, in the camera unit A(mn).

The thicknesses D of the object 72b which cause the phase differences are different for respective plurality of camera units A, and within the wavelength range to be measured, respective types of refractive index dispersion are assumed to be sufficiently small. Further, the object 72b may also be a reflection type, for example, with a 45-degree incidence. In addition, for the configuration of the reflection type of a 45-degree incidence, see Japanese Patent No. 5078004. In addition, in FIG. 4, while the colors of the apples as the objects illustrated in the upper part in FIG. 4 are the same, the colors of the apples illustrated in the lower part in FIG. 4 are not the same, which indicate that the interference images in which different wavelengths are emphasized are captured by the respective camera units A.

<Signal Processing Method>

Next, with reference to FIG. 6, a signal processing method for generating an HSI from the interference images captured by the respective plurality of camera units A in the camera array 51, and outputting spectroscopic spectral data in units of pixels will be described.

Further, here, the number of pixels of respective camera units A included in the camera array 51 is assumed to be, for example, a QVGA (320×240 pixels). Further, for simplicity of explanation, it is assumed that the object is present at infinity and that the parallax for each camera unit is regarded as zero. In addition, pixels at a predetermined position in the interference images captured by respective camera units A constituting the camera array 51 are assumed to be the pixels at the same position within each of the interference images.

Figure 6:
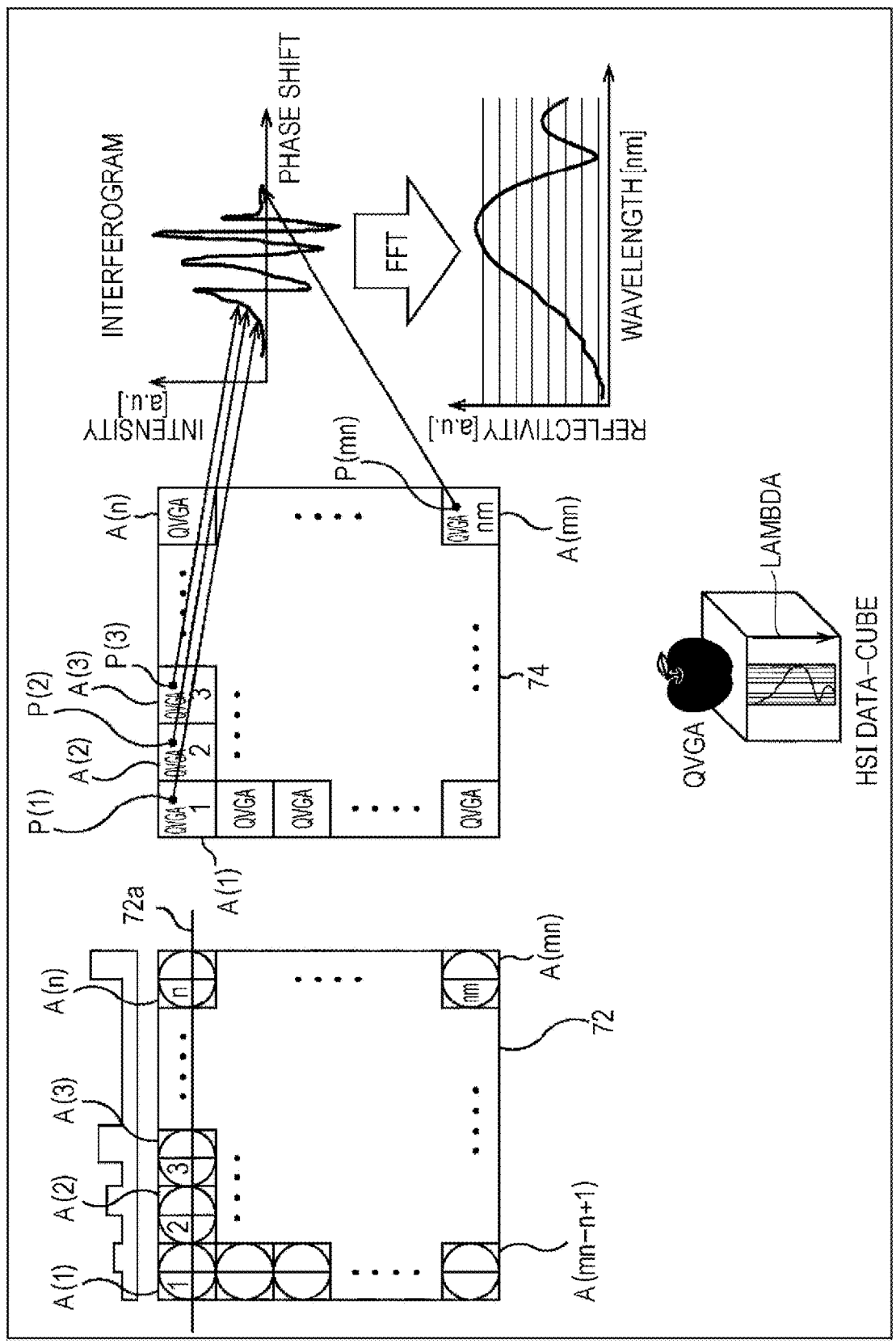
FIG. 6 is a diagram illustrating a signal process.

As illustrated in the left part and the center part of FIG. 6, if the pixels at the same position in the respective interference images are distributed according to the phase differences, for example, the interferogram illustrated in the upper right part of FIG. 6 is obtained.

In other words, the pixels P(1) to P(mn) at the same position in the respective camera units A(1) to A(mn) in FIG. 6 are read, and the distribution of the received light intensities of the pixels P(1) to P(mn) according to the phase difference corresponding to each image is the interferogram illustrated in the upper right part of FIG. 6. Here, in FIG. 6, the horizontal axis represents a phase difference (Phase shift), and the vertical axis represents the received light intensity (Intensity).

Accordingly, the interferograms of the same number as the number of pixels corresponding to QVGA (320×240 pixels) are obtained.

The spectroscopic spectrum of each pixel corresponding to each image of the camera unit is obtained as illustrated in the lower right part of FIG. 6 by performing fast Fourier transform (FFT) on the interferogram which is obtained individually for each pixel position. In other words, in the lower right part of FIG. 6, the horizontal axis represents a wavelength, and the vertical axis represents a reflectivity.

Accordingly, through such a process, spectroscopic spectrum for the image of QVGA (320×240 pixels) is obtained. In the following description, the spectroscopic spectral data for each pixel of the image of QVGA (320×240 pixels) obtained in this manner is collectively referred to as an HSI Data cube. In addition, the image of an apple that is shown in the lower center part of FIG. 6 and a cube thereunder imitate the hyper spectral imaging (HSI) data cube configured with spectroscopic spectral data of each pixel in an image of which the object is an apple.

For example, the number of camera units A is 8×8 in the horizontal direction×the vertical direction in the camera array 51, and when a total is 64, the number of all of the pixels is 64×QVGA=4.9 M pixels. Accordingly, it is the number of pixels which can be realized in a current commercial solid imaging element. Further, for example, if the cell size of the imaging element is assumed to be 3 micrometers, the sizes in the horizontal direction and vertical direction of the camera unit A are respectively about 1 mm, when the number is 8×8, since the entire size in the horizontal direction and the vertical direction respectively fit within about 10 mm, it is possible to sufficiently achieve miniaturization in practice. In fact, for example, the signal process is performed for each QVGA area of 8×8 on a single CMOS image sensor (CIS) described above of 4.9 M pixels or more, such that a process is performed for each area corresponding to 64 camera units A.

<Specific Design Method>

Next, examples of the number of camera units A (the number of a plurality of images which are set in the lens arrays 71 and 73), and a method of designing a phase difference step in the phase difference array will be specifically described.

Figure 7:
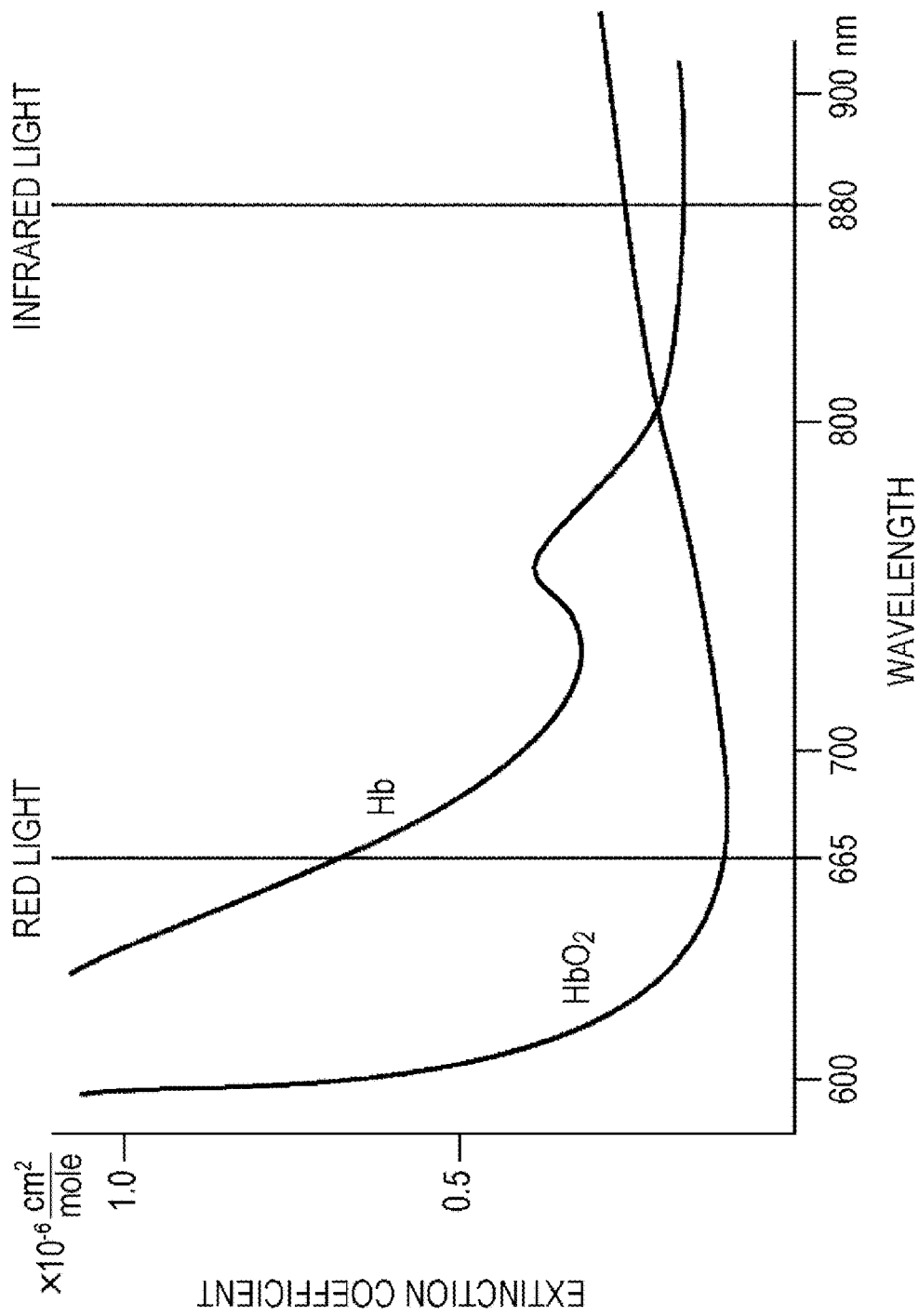
FIG. 7 is a diagram illustrating a method of designing the camera array.

For example, as illustrated in FIG. 7, the spectral absorption characteristics of oxygenated hemoglobin (HbO$_2$) and reduced hemoglobin (Hb) in the blood are assumed as the measurement objects. The necessary measurement wavelength resolution is determined by the kurtosis of spectral characteristics. In FIG. 7, the horizontal axis represents a wavelength, and the vertical axis represents an absorption coefficient.

For example, when measuring the spectral absorption characteristics of the oxygenated hemoglobin (HbO$_2$) and the reduced hemoglobin (Hb) in the blood illustrated in FIG. 7 by the HSI, if the necessary wavelength resolution is assumed as an extreme value detection of near 750 nm of the reduced hemoglobin (Hb), the wavelength resolution (deltalambda) of about 25 nm is necessary from the sampling theorem. Then, if assuming that the necessary minimum wavelength (lambdamin) is 600 nm, a focused central wavelength (lambdac) is 665 nm which is the absorption extreme value of oxygenated hemoglobin (HbO$_2$). The phase difference step is lambdamin/2=600/2=300 nm from the sampling theorem of wavelength resolution.

The wavelength resolution obtained from the sampling theorem in a Fourier domain is (lambdac)$^2$/phase difference range. Since the necessary wavelength resolution is 25 nm, the phase difference range is (lambdac)$^2$/0.025=(0.665)$^2$/0.025=17.7 micrometers. In addition, the number of phase steps (in the lens arrays 71 and 73, the number of images having the same captured imaging area, in other words, the number of camera units A) is equal to or greater than the phase difference range/phase difference step=17.7/0.3=59. In other words, a phase difference array in which 8×8=64 rows of phase differences are formed at steps of 300 nm from 0 nm to 17.7 micrometers by the air conversion and 8×8 lens arrays are configured.

Accordingly, since the phase difference is 300 nm by the air conversion in order to form such a phase difference array, when forming the object 72b illustrated in FIG. 5 using a normal transparent resin material having a refractive index n=1.5, 8×8=64 rows are formed at steps of 600 nm from 0 nm to 35.4 micrometers.

<Blood Test Process>

Figure 8:
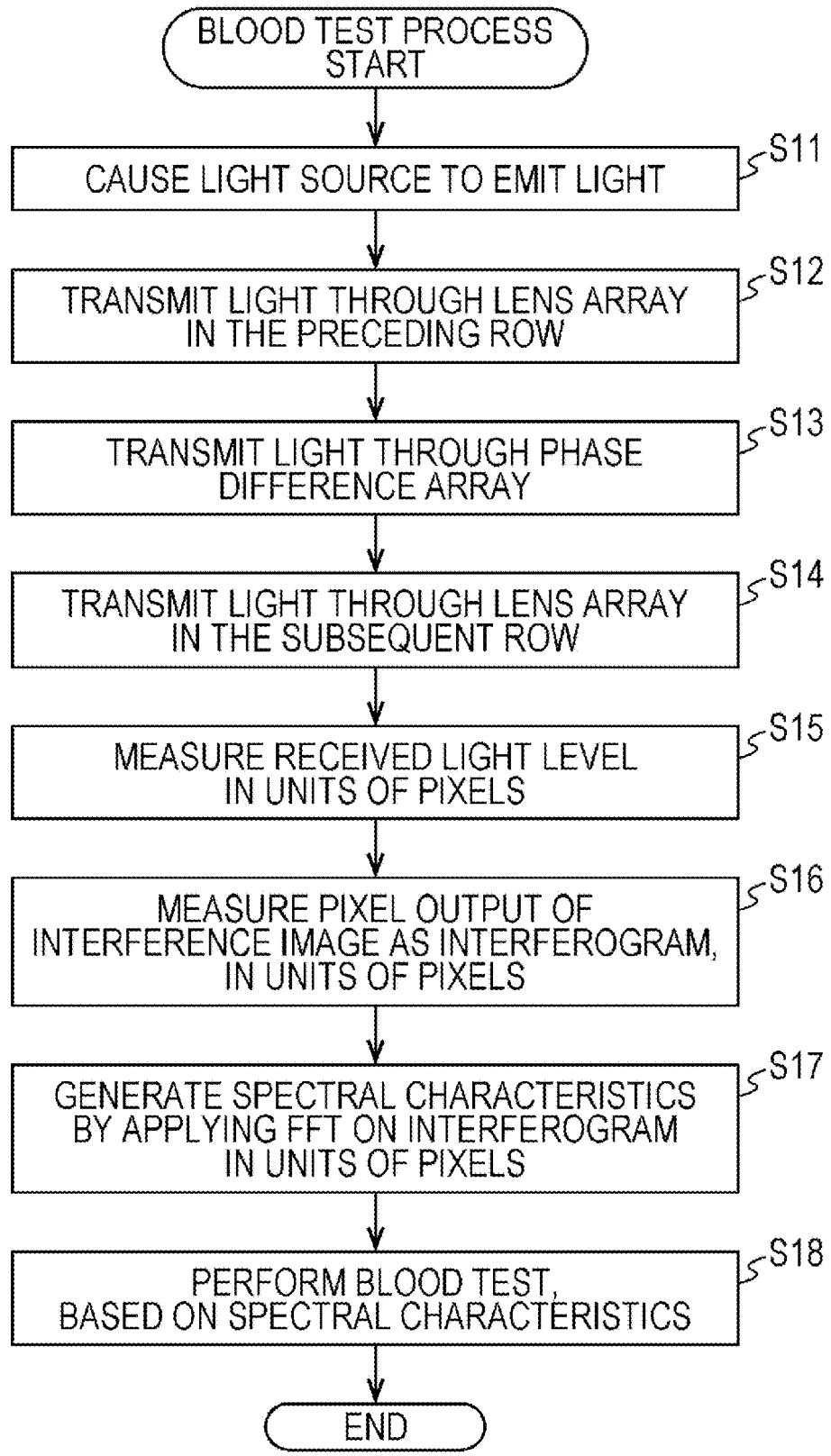
FIG. 8 is a flowchart illustrating a blood test process.

Next, a blood test process using the blood test apparatus of FIG. 1 will be described with reference to the flowchart of FIG. 8.

In step S11, the signal processing unit 52 causes the light source 32 to emit light, and project the light to an area in which the artery 12a and the vein 12b of the arm 12 to be detected may be present.

In step S12, each lens in the array 71 provided in the preceding row in the light incident direction transmits the incident light as the light corresponding to each camera unit A, such that the incident light is converted into sets of parallel light that are incident on the phase difference array 72.

In step S13, the phase difference array 72 causes the light flux with the added phase difference to be incident on the lens array 73, with respect to each camera unit A.

In step S14, each lens in the array 73 provided in the subsequent row in the incident direction of light passes the respective light fluxes incident from the phase difference array 72 so as to be imaged on the imaging element array 74.

In step S15, the light receiving level of the interference image in each pixel of the imaging element array 74 is detected, and a pixel output which is a detection result is output to the signal processing unit 52, in units of the camera units A.

In step S16, the signal processing unit 52 generates the data constituting the interferogram in units of pixels, based on the pixel signal in units of the camera units A that is supplied from the imaging element array 74.

In step S17, the signal processing unit 52 performs Fast Fourier transform (FFT) on data obtained as an interferogram, and generates the hyper spectral imaging (HSI) data cube configured with data of the spectral spectrum for each pixel.

In step S18, signal processing unit 52 extracts the spectroscopic spectra of the artery portion and the vein portion from the HSI Data cube which is spectroscopic spectral data, analyzes predetermined components in the blood, and displays the analyzed values on the display unit 33 as the test results. The HSI can change whether the analysis target is artery blood or vein blood, or whether to use both data, depending on the contents to be analyzed. For example, the signal processing unit 52 detects the oxygen concentration and the lipid level in the blood, based on the spectroscopic spectral data of the artery portion, detects the blood glucose level and the like, based on the spectroscopic spectral data of the vein portion, and displays the detected values on the display unit 33 as an analysis result.

Since it is possible to obtain the spectroscopic spectrum by performing fast Fourier transform on the interference image by the above process, there is no energy loss such as a spectral filter, and it becomes possible to realize an HSI of high sensitivity. In addition, since a light source of a large output is not necessary by such a configuration, it is possible to miniaturize the configuration of the entire apparatus. Further, since it is possible to capture simultaneously the spectroscopic spectral data and all pixels in the image at high sensitivity, it is possible to realize capturing of a moving image by the HSI, by an inexpensive configuration without using a special material and a moving unit.

<With Respect to Manufacturing Method>

Figure 9:
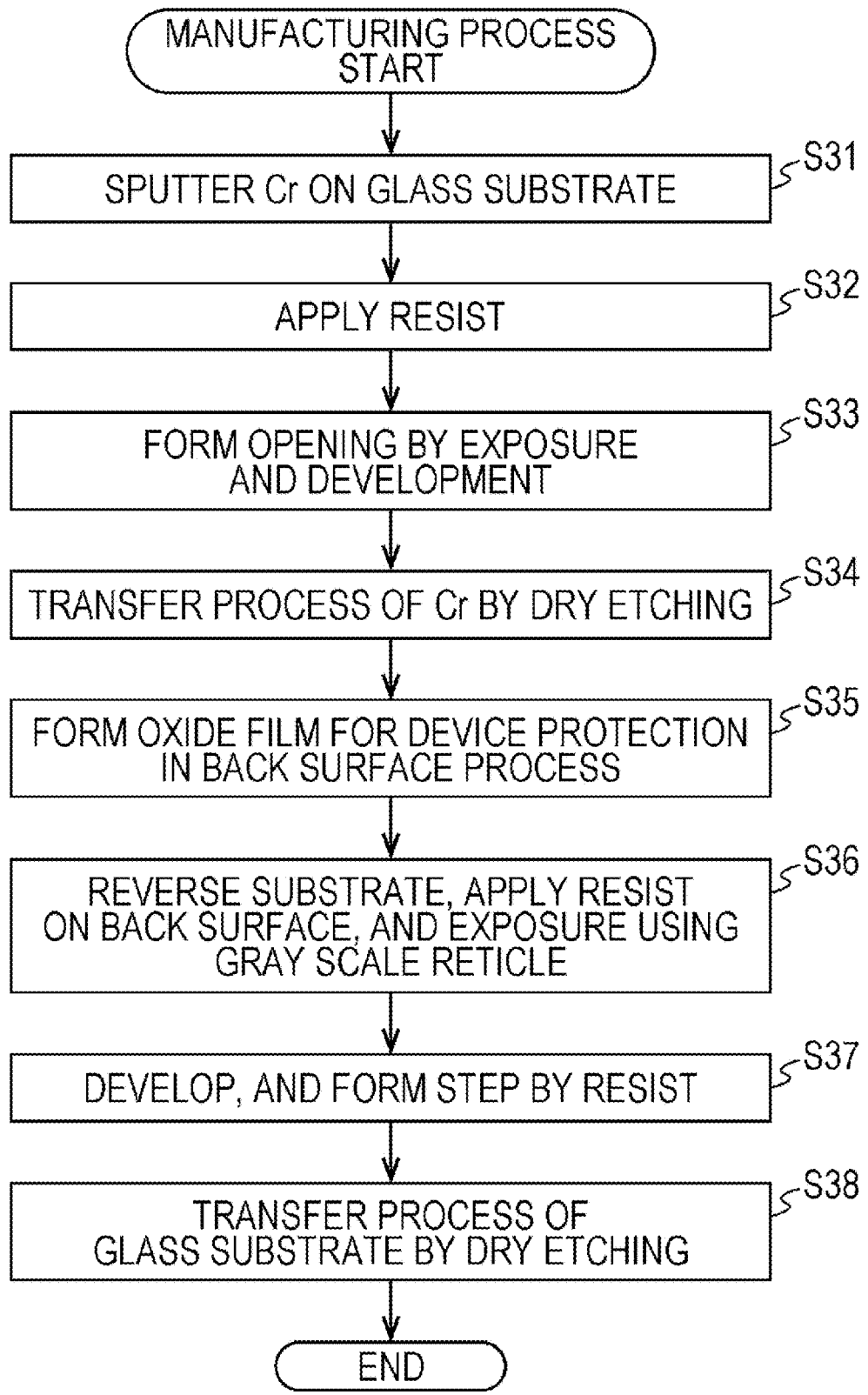
FIG. 9 is a flowchart illustrating a manufacturing process of a phase difference array.

Next, a manufacturing method of the phase difference array 72 will be described with reference to the flowchart of FIG. 9.

Figure 10:
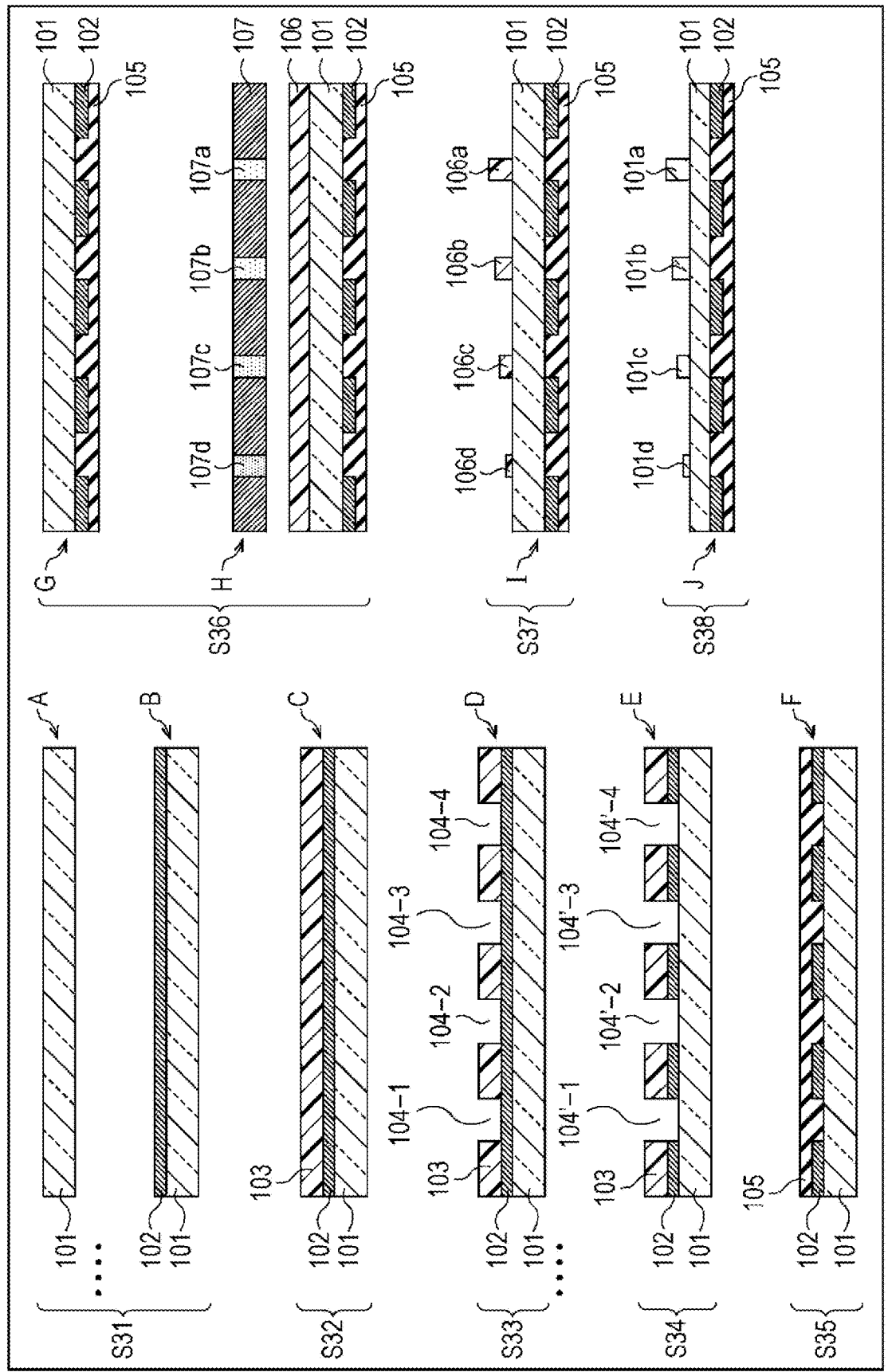
FIG. 10 is a diagram illustrating a manufacturing process of the phase difference array.

In step S31, as illustrated in a state B in FIG. 10, a chromium Cr layer 102 is formed by sputtering on the upper surface of the glass substrate 101, illustrated in a state A in FIG. 10.

In step S32, as illustrated in a state C in FIG. 10, a resist layer 103 is formed on the upper surface of the chromium Cr layer 102.

In step S33, as illustrated in a state D in FIG. 10, openings 104-1 to 104-4 of a circular aperture shape that determine the numerical aperture of the number of the above-mentioned camera array (numerical aperture (NA) or a F-value) are formed, by exposure and development. Further, the example of the case of openings 104-1 to 104-4 of four is illustrated, but it is only an example, and in the following, the case of openings 104-1 to 104-4 of four will be described.

In step S34, as illustrated in a state E in FIG. 10, the chromium Cr layer 102 is subjected to a transfer machining, by dry etching so as to form openings 104'-1 to 104'-4. In addition, thereafter, without being illustrated, the resist layer 103 is removed.

In step S35, as illustrated in a state F in FIG. 10, for the device protection in the back process, a silicon oxide film 105 and the like are formed.

In step S36, as illustrated in a state G in FIG. 10, the glass substrate 101 is inverted.

Further, as illustrated in a state H in FIG. 10, a resist layer 106 is formed on the back surface of the glass substrate 101. Further, the resist layer 106 is exposed using a grayscale reticle (gray-scale photomask). For the exposure by grayscale reticle, see Japanese Patent No. 429643 of the applicant.

In step S37, as illustrated in a state I in FIG. 10, protrusions 106a to 106d are formed in the resist layer 106 by the development.

In step S38, as illustrated in a state J in FIG. 10, protrusions 101a to 101d corresponding to the object 72b are formed on the glass substrate by dry etching. Thereafter, if the oxide film 105 is removed, the phase difference array 72 is completed. In other words, the protrusions 101a to 101d are formed as the semicircular object 72b in FIG. 5.

Further, in the case of using a permanent resist, in step S37, when steps 106a to 106d are formed in the resist layer 106, the process is terminated, and the process of step S38 is skipped. In other words, in this case, protrusions 106a to 106d are formed as a semicircular object 72b in FIG. 5.

By the above process, since the phase difference array 72 can be processed in a semiconductor process without using a special material, it becomes possible to realize a cost reduction of the camera array 51. Further, since it is possible to process a signal by area division in the imaging element, by forming the array structure on a common imaging element, the imaging element can substantially be a single element, therefore it is possible to realize cost reduction, and an increase in processing speed.

In addition, in the above, the description has been made about the example of the application to the blood test apparatus that detects the components such as the oxygen concentration, lipid level, and the blood glucose level by using the spectroscopic spectral data obtained by the HSI Data cube, but as long as it can perform detection by using the spectroscopic spectral data, it may also be applied to other devices, for example, it may also be applied to various measurement technologies such as health care, beauty treatment, agriculture, food hygiene, and environmental measurements.

Further, since the description has been made about the case where the object is present at the infinity, the description has been made that the parallax for each camera unit can be ignored, in fact, the parallax occurs in each camera unit. There is an assumption that an image to be captured by each camera unit is the same, it is possible to use the image captured by, for example, the camera unit in the vicinity of the center of the camera array 51, by cutting the image for each camera unit, and performing a parallax correction referred to as an XY shift, therefore it is possible to improve the accuracy the HSI image.

<First Modification>

Figure 11:
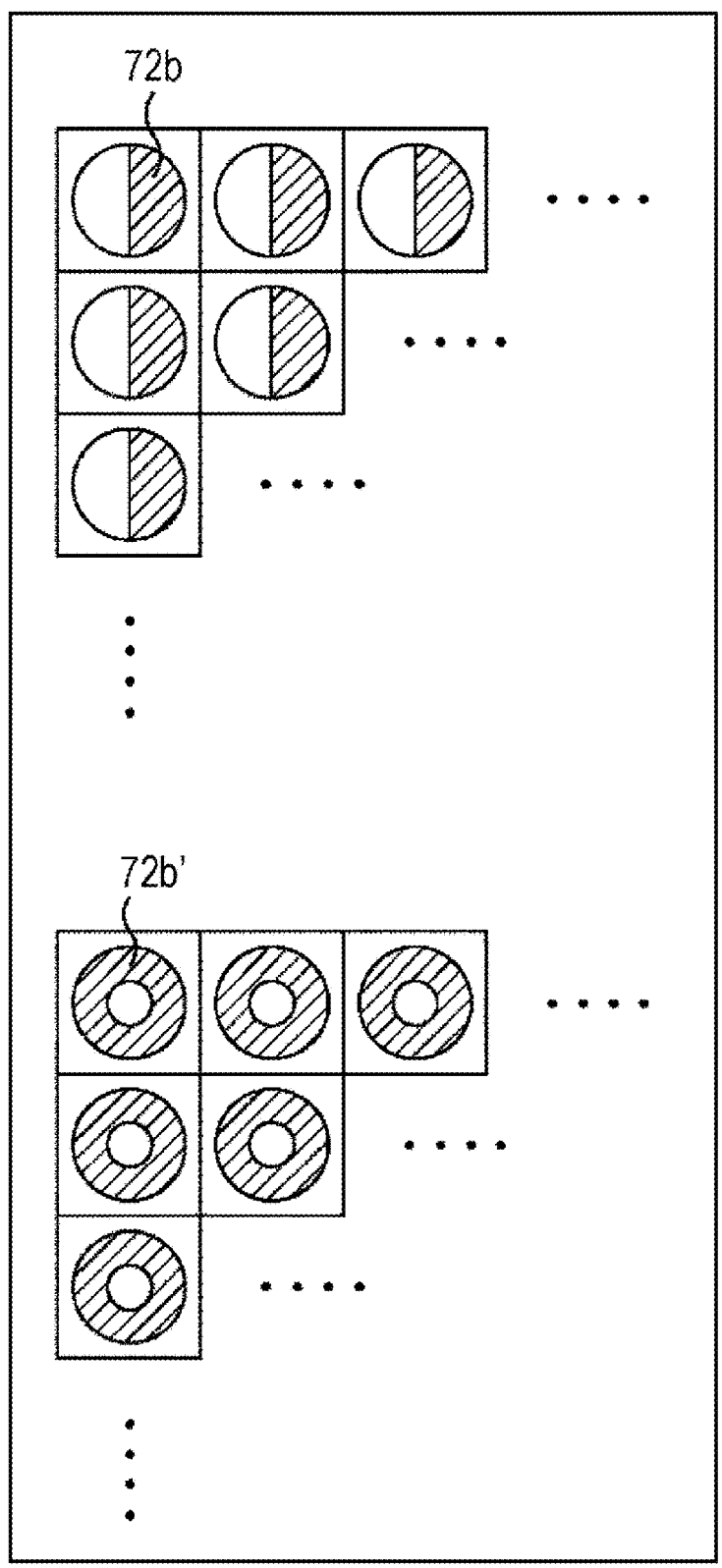
FIG. 11 is a diagram illustrating another configuration example of a phase difference array, which is a first modification.

In the above, the description has been made about the example of providing the optical path difference by the object 72b while being divided into the right and left in FIG. 11, as illustrated in the upper portion of FIG. 11, the area where the object 72b is provided and the area where the object 72b is not provided may be provided in the upper and lower parts, or the right, left, upper, and lower parts in an oblique direction, in addition to the right and left parts.

Further, as illustrated in the lower portion of FIG. 11, an area where the object 72b' is not provided may be set in the center part so as to provide the object 72b' in a cylindrical shape, in the area of each camera unit A.

<Second Modification>

Figure 12:
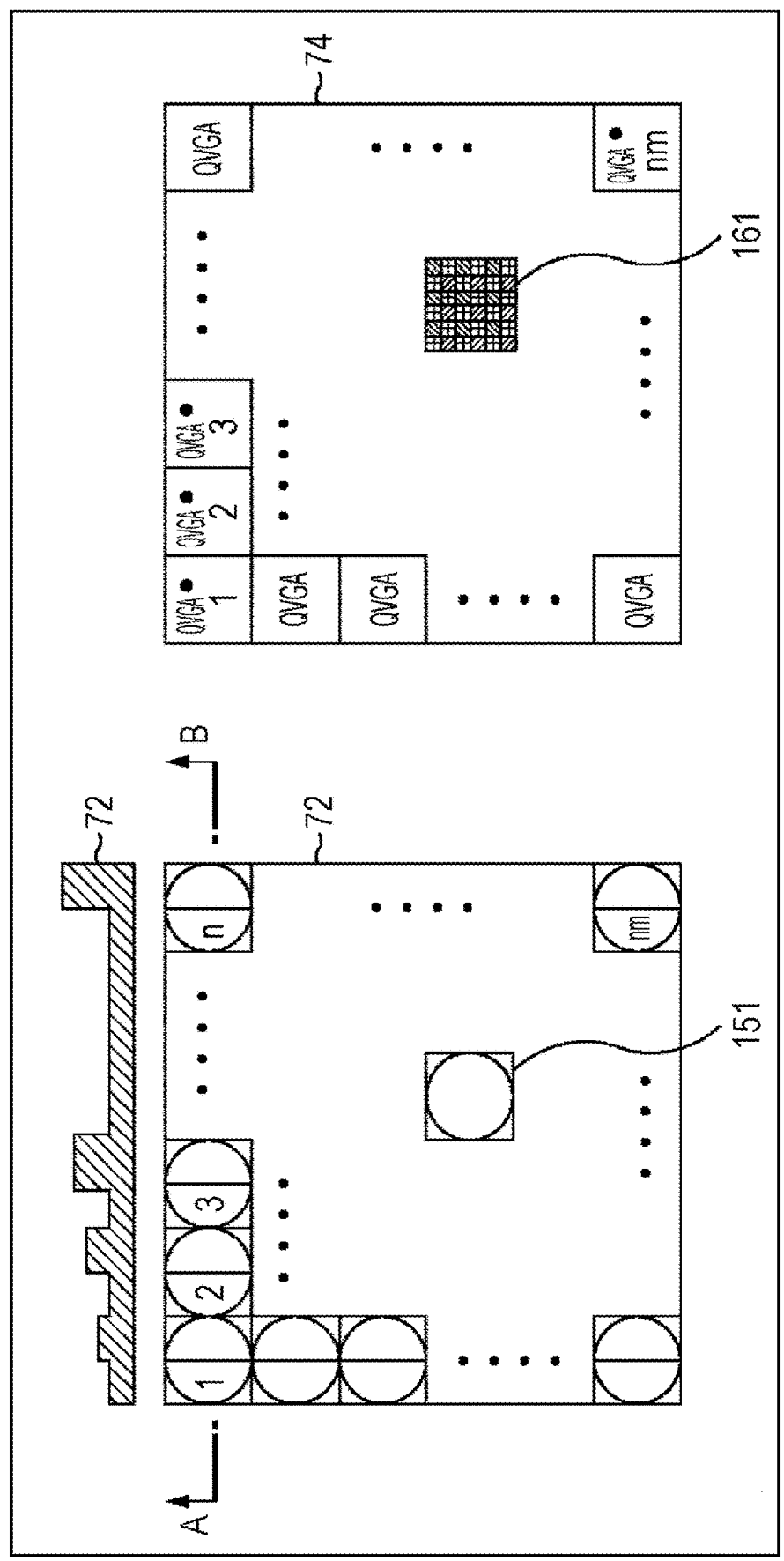
FIG. 12 is a diagram illustrating a configuration example of providing an area for capturing a color image, in an imaging element array, which is a second modification.

In the above, the description has been made about examples of acquiring only the HSI by the camera array 51, but as illustrated in the right part of FIG. 12, an RGB color filter 161 may be set for one of the camera units, therefore it is possible to generate a red image, a green image, and a blue image by de-mosaicing so as to capture a general color image. In this case, in the phase difference array 72, in the area of the corresponding camera unit A, as illustrated in the left part of FIG. 12, the non-phase difference array 151 is configured in which the object 72b is not provided such that the phase difference does not occur in the entire area. In addition, in the upper left part of FIG. 12, cross-section AB of the phase difference array 72 in the lower left part is illustrated. Further, the number assigned to each square is an identification number of the camera unit A.

In addition, areas other than the area where the non-phase difference array 151 is provided in the imaging element array 74 are used for the process for obtaining the HSI Data cube, and the area where the non-phase difference array 151 is provided is used for the process of generating a color image.

With this configuration, it becomes possible to simultaneously obtain the color image and the HSI Data cube in the same imaging area, and use the color image and the HSI while superimposing them. Further, it is desirable that the color image is in the vicinity of the center of the camera array 51.

Figure 13:
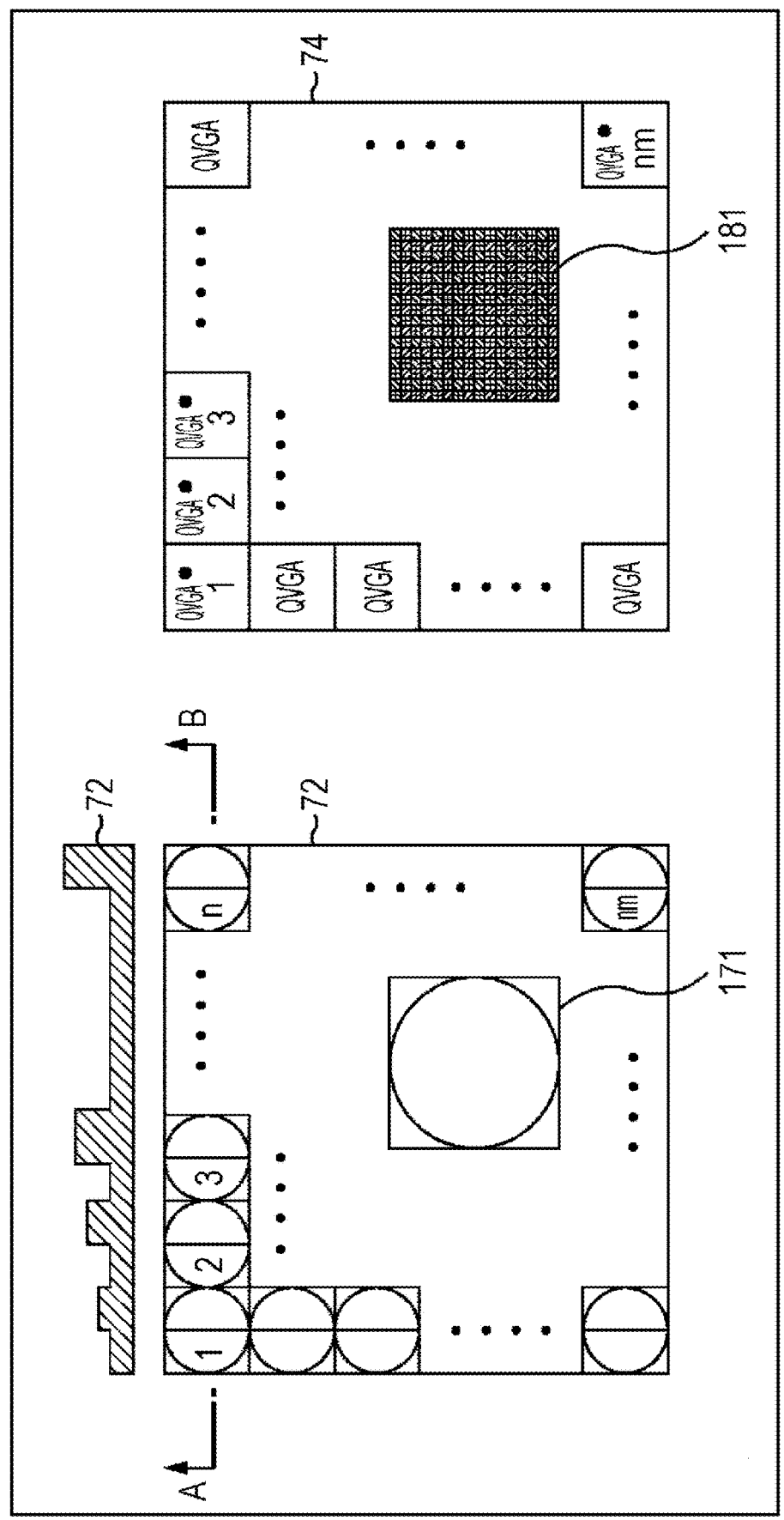
FIG. 13 is a diagram illustrating a configuration example of further enlarging the area for capturing the color image, in the second modification.

Further, as illustrated in the left part of FIG. 13, a non-phase difference array 171 is provided in an area for generating a color image of the area of 2×2 times the area of the camera unit in the horizontal direction and vertical direction, as illustrated in the right part of FIG. 13, a color filter 181 of the same size may be provided. In this case, it is possible to generate the HSI Data cube while generating an image of the VGA (640×480 pixels). Even in this case, it is desirable that the color image is in the vicinity of the center of the camera array 51. Further, the color filter may be one other than the three colors of RGB, and it is also possible to capture the monochrome image containing only luminance. Further, if the number of pixels of SXGA (1280×960 pixels) is allocated as necessary, it is possible to provide a general color image of an HD quality.

<Third Modification>

The description has been made about examples of acquiring the HSI Data cube, or the HSI Data cube and the color image, and respective camera units are provided in the camera array 51 while the respective ends are separated in the horizontal direction and vertical direction, but stereo cameras as the camera units are provided in the respective ends, therefore it is possible to obtain a so-called depth image including depth information regarding depth distances in units of pixels in the camera unit. This makes it possible to simultaneously obtain the spectral information and depth information of the object.

Figure 14:
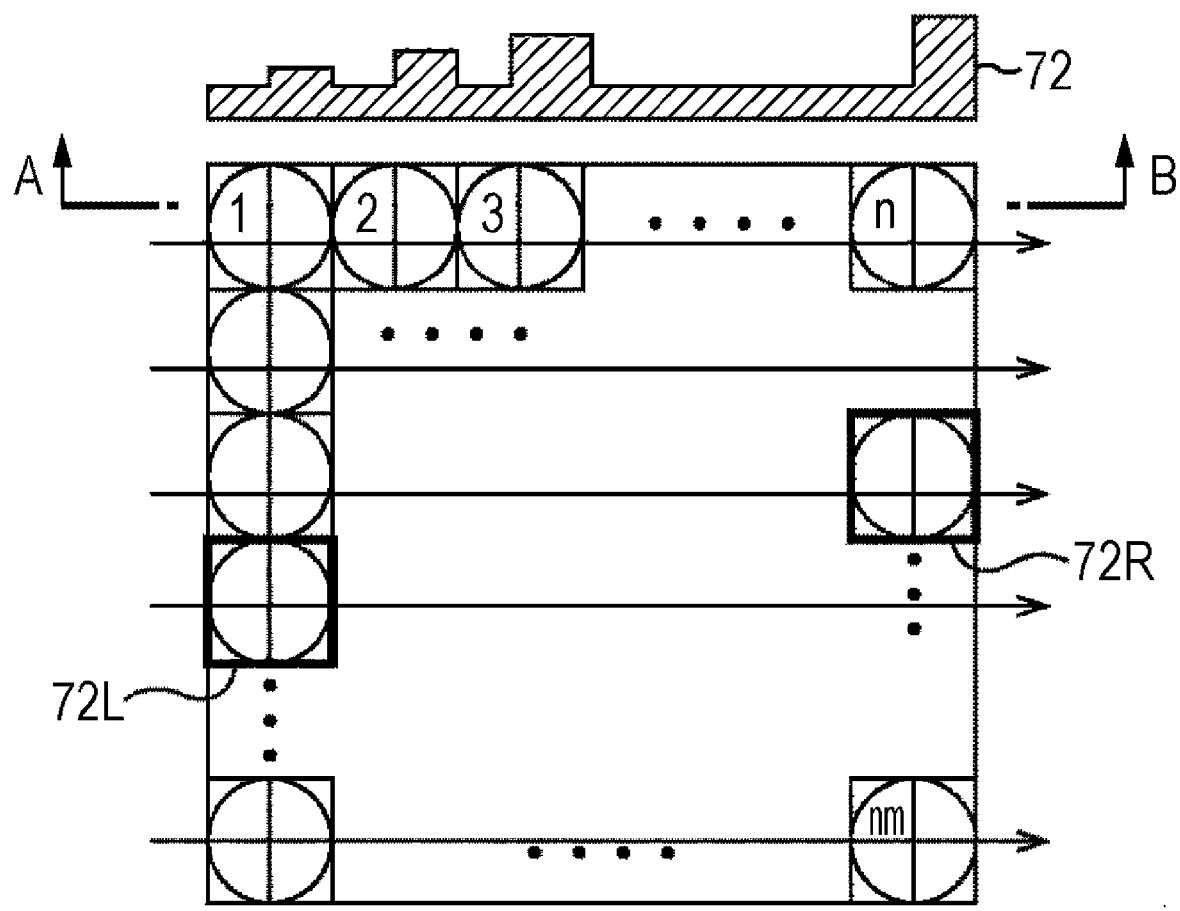
FIG. 14 is a diagram illustrating an example of generating a depth image by using a stereo image, which is a third modification.

More specifically, as illustrated by arrows in FIG. 14, it is configured in that with respect to the phase difference, the thicknesses D of the objects 72b in the phase difference array 72 continuously and sequentially change towards the right direction in the horizontal direction. This makes it possible to obtain a depth image from the parallax between monochrome images which are obtained by the camera module A corresponding to the phase difference array 72R present in the right end portion of FIG. 14 and the camera module A corresponding to the phase difference array 72L present in the left end portion below one row. In addition, if the phase difference array 72R and the phase difference array 72L are in the height order of the thickness D, they are adjacent to each other, and thus the amount of change in phase difference is significantly small. Therefore, the influence on the depth distance by the parallax is very small. In addition, it is natural to use the images before the parallax correction is performed on the phase difference arrays 72R and 72L for obtaining the depth image in such a manner.

<Fourth Modification>

In the above, the description has been made about the example of simultaneously imaging the HSI image and the depth image, but it may be possible to obtain polarization information.

Figure 15:
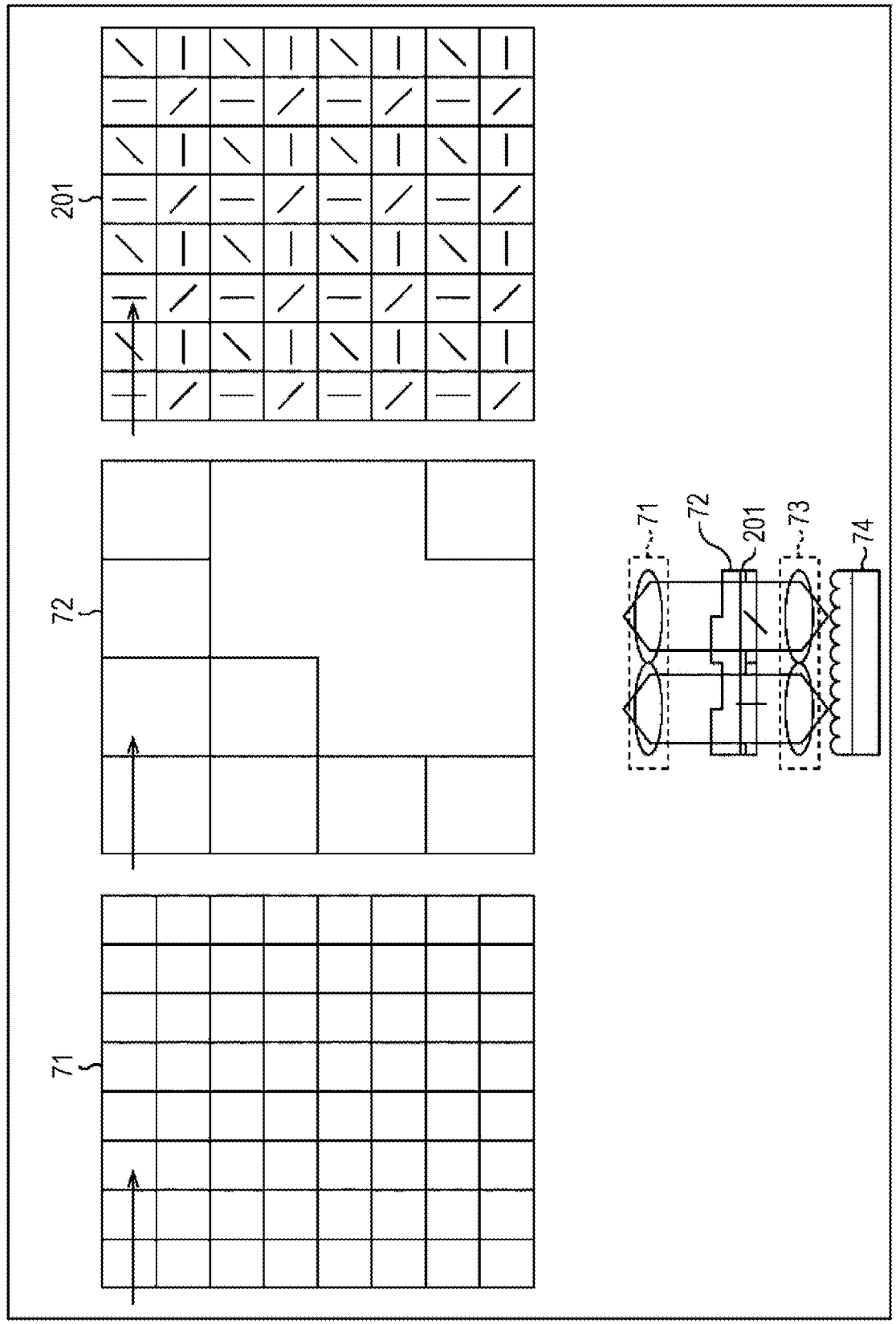
FIG. 15 is a diagram illustrating an example of obtaining a polarization state by using four types of the polarizers, which is a fourth modification.

In other words, as illustrated in the lower center part of FIG. 15, a polarizer array 201 is provided between the phase difference array 72 and the lens array 73, therefore it is possible to obtain polarization information.

More specifically, as illustrated in the upper left part of FIG. 15, when the camera units A are set in a square shape, as illustrated in the center part of FIG. 15, the phase difference array 72 which is the same optical path is set in a unit of a range of 2×2 pieces.

Further, as illustrated in the upper right part of FIG. 15, in the polarizer array 201, polarizers which differ by 45 degrees are disposed in 2×2 camera units present in the area of the phase difference array 72 which is the same optical path.

In general, in the polarizer, Stokes parameters for representing the polarization state or Jones vectors are obtained by analyzing the polarization components of four orientations. Therefore, the Stokes parameters or the Jones vectors of each pixel are obtained, based on information regarding the camera units of the polarizers of the four orientations in the area of the phase difference array 72 which is the same optical path, by, for example, the signal processing unit 52, therefore it is possible to obtain the polarization state in units of pixels.

If the size of the camera unit A is a QVGA pixel, the polarizing sheet which is formed by a general rolling process is cut to the size of the camera unit area, such as the size of about a 1 mm square, and the orientations of the cut sheets are changed, therefore it is possible to realize the configuration illustrated in FIG. 15.

With this configuration, it becomes possible to simultaneously obtain and superimpose the HSI image including the spectroscopic spectrum, the depth image, and the polarization image.

However, the series of processes described above can be performed by hardware, but can also be performed by software. When the series of processes are performed by software, programs constituting the software are installed in a dedicated hardware built-in computer, or for example, a general-purpose personal computer capable of executing various functions by installing various programs, from the recording medium.

FIG. 16 is a diagram illustrating a configuration example of a general-purpose personal computer. A central processing unit (CPU) 1001 is built into the personal computer. The CPU 1001 is connected to an input and output interface 1005 through a bus 1004. A read only memory (ROM) 1002 and a random access memory (RAM) 1003 are connected to the bus 1004.

An input unit 1006 including input devices such as a keyboard and a mouse through which the user inputs operation commands, an output unit 1007 that outputs processing operation screens and images resulting from processes on a display device, a storage unit 1008 including a hard disk drive that stores programs and various types of data, and a communication unit 1009 including a local area network (LAN) adapter that executes a communication process through a network represented by the Internet are connected to the input and output interface 1005. Further, a drive 1010 that reads and write data to a removable media 1011 such as a magnetic disk (including a flexible disk), an optical disk (including a compact disc-read only memory (CD-ROM), and a digital versatile disc (DVD)), a magneto-optical disk (including a mini disc (MD)), or a semiconductor memory is connected to the input and output interface 1005.

The CPU 1001 performs various processes according to the program stored in the ROM 1002, or the program which is read from the removable media 1011 such as the magnetic disk, the optical disk, the magneto-optical disk, or the semiconductor memory and installed in the storage unit 1008, and read from the storage unit 1008 and loaded in the RAM 1003. The RAM 1003 appropriately stores data and the like necessary for the CPU 1001 to execute various processes.

In the computer configured as described above, a series of processes described above are performed by the CPU 1001 loading, for example, the program stored in the storage unit 1008 on the RAM 1003 and executing the program, through the input and output interface 1005 and the bus 1004.

The program that the computer (CPU 1001) executes may be provided by being recorded, for example, on the removable media 1011 as package media or the like. Further, the program may be provided through a wired or wireless transmission medium such as a local area network, the Internet, and digital satellite broadcasting.

In the computer, the program may be installed in the storage unit 1008, through the input and output interface 1005, by mounting the removable media 1011 in the drive 1010. Further, the program may be received by the communication unit 1009 and installed in the storage unit 1008, through a wired or wireless transmission medium. Alternatively, the program may be installed in advance in the ROM 1002 or the storage unit 1008.

In addition, the program that the computer executes may be a program in which processes are performed chronologically in the order described in the specification, or a program in which processes are performed in parallel or at a necessary timing, such as when a call is made.

In the present specification, a system refers to the collection of a plurality of components (devices, modules (parts), and the like), and it does not matter whether all the components are in the same housing. Thus, a plurality of devices which are housed in separate housings and connected through a network, and one device including a plurality of modules which are housed in one housing are both the system.

In addition, embodiments of the present technology are not limited to the embodiments described above, and various modifications are possible in a scope without departing from the spirit of the present technology.

For example, the present technology may take a cloud computing configuration in which one function is shared by a plurality of devices to be processed jointly through the network.

Further, each step described in the flowchart described above may be performed by being shared by a plurality of devices, as well as by one device.

Further, when one step contains a plurality of processes, a plurality of processes included in the one step may be performed by being shared by a plurality of devices, as well as by one device.

In addition, the present technology may have the following configurations.

(1) An imaging device, comprising:
a phase difference array with a plurality of elements, wherein the phase difference array is configured to provide different optical paths for light included within at least some of a plurality of sets of light beams; and
an imaging element array including a plurality of imaging elements, wherein at least one of the imaging elements is configured to receive one of the sets of light beams from the phase difference array.

(2) The imaging device according to (1) or (2), further comprising: an objective lens array, wherein the objective lens array includes a plurality of objective lenses, and wherein the objective lens array is configured to provide the plurality of sets of light beams to the phase difference array.

(3) The imaging device according to (2), wherein the plurality of sets of light beams provided by the objective lens array are cylindrical parallel light beams.

(4) The imaging device according to any one of (1) to (3), wherein at least some of the elements of the phase difference array are configured to generate an optical path difference between a first portion of a light beam incident on a first part of the element and a second portion of the light beam incident on a second part of the element.

(5) The imaging device according to (4), wherein for the at least some of the elements of the phase difference array a thickness of the first part of the element is different than a thickness of the second part of the element.

(6) The imaging element according to (5), wherein the first part of the element has a semicircular area.

(7) The imaging device according to (5), wherein the first part of the element has a cylindrical area.

(8) The imaging device according to (5), wherein the thickness of the first part of the element increases from an element at a first end of the phase difference array to an element at a second end of the phase difference array.

(9) The imaging device according to any one of (1) to (8), further comprising: a polarizer array, wherein the polarizer array includes four different types of polarizers that differ from one another by at least 45 degrees.

(10) The imaging device according to any one of (1) to (9), further comprising: an imaging lens array including a plurality of imaging lenses, wherein the imaging lens array is positioned between the phase difference array and the imaging element array.

(11) The imaging device according to (10), wherein the imaging lenses of the imaging lens array image the plurality of sets of light beams onto at least some of the imaging elements.

(12) The imaging device according to any one of (1) to (11), wherein each of the imaging elements includes a plurality of pixels.

(13) The imaging device according to any one of (1) to (12), wherein light from a first area of an imaged object is included in a first one of the sets of light beams, and wherein light from the first area of the imaged object is included in a second one of the sets of light beams.

(14) A detection apparatus, comprising: a connecting structure; a light source, wherein the light source is connected to the connecting structure; an enclosure, wherein the enclosure is connected to the connecting structure, and wherein the enclosure includes: a phase difference array with a plurality of elements, wherein the phase difference array is configured to provide different optical paths for light included within at least some of a plurality of sets of light beams; an imaging element array including a plurality of imaging elements, wherein at least one of the imaging elements is configured to receive one of the sets of light beams from the phase difference array; a display, wherein the display is connected to the connecting structure, and wherein the display is operable to display detection information generated from data provided by the imaging element array.

(15) The detection apparatus according to (14), further comprising: an objective lens array, wherein the object lens array includes a plurality of objective lenses, and wherein the objective lens array is configured to provide the plurality of sets of light beams to the phase difference array.

(16) The detection apparatus according to (15), wherein the plurality of sets of light beams provided by the objective lens array are cylindrical parallel light beams.

(17) The detection apparatus according to any one of (14) to (16), wherein at least some of the elements of the phase difference array are configured to generate an optical path difference between a first portion of a light beam incident on a first part of the element and a second portion of the light beam incident on a second part of the element.

(18) The detection apparatus according to (17), wherein for at least some of the elements of the phase difference array a thickness of the first part of the element of the phase difference array is different than a thickness of the second part of the element of the phase difference array.

(19) The detection apparatus according to (18), wherein the first part of the element has a semicircular area.

(20) The detection apparatus according to (18), wherein the first part of the element has a cylindrical area.

(21) The detection apparatus according to (18), wherein a thickness of the first part of the element increases from an element at a first end of the phase difference array to an element at a second end of the phase difference array.

(22) The detection apparatus according to any one of (14) to (21), wherein the enclosure further includes: a polarizer array, wherein the polarizer array includes four different types of polarizers that differ from one another by at least 45 degrees.

(23) The detection apparatus according to any one of (14) to (22), wherein the connecting structure is a belt.

(24) A method for detecting a physical property, comprising: emitting light onto an object; receiving light from the object at a plurality of phase difference elements included in a phase difference array, wherein at least some of the phase difference elements generate a phase difference from the light incident on the phase difference elements; receiving light from the phase difference elements at an imaging element array; displaying information obtained from hyperspectral imaging (HIS) data based on output signals of the imaging element array.

(25) An imaging device including
an imaging element array that captures a same imaging area, as a plurality of unit images; and
a phase difference array that causes respective different optical path differences in a portion of respective imaging areas of the plurality of unit images which are captured by the imaging element array.

(26) The imaging device according to (25),
wherein the phase difference array includes a filter that causes the optical path differences in a semicircular shape for the respective imaging areas, and
wherein the optical path differences are different for the respective imaging areas of the plurality of unit images.

(27) The imaging device according to (25) or (26),
wherein a filter constituting the phase difference array has sufficiently small refractive index dispersion in a wavelength range to be measured, or is a reflection type with incidence of 45 degrees.

(28) The imaging device according to any one of (25) to (27),
wherein the imaging element array captures images caused for the respective imaging areas by the phase difference array, as interference images.

(29) The imaging device according to (28), further including
a signal processing unit that generates an interferogram from output data of pixels at the same position of the respective interference images that are captured for the respective imaging areas by the imaging element array, and calculates spectral characteristics of the respective pixels as hyper spectral imaging (HSI) data cubes by performing Fourier transform on the interferogram.

(30) The imaging device according to (29),
wherein a phase difference of the phase difference array is set so as to monotonically increase or monotonically decrease, in a predetermined direction of the imaging areas which are arranged consecutively, and
wherein the signal processing unit generates a depth image by using an image of an imaging area at one end and an image of an imaging area at the other end, in the predetermined direction of the phase difference array, as a stereo image.

(31) The imaging device according to any one of (25) to (30),
wherein optical elements in the respective imaging areas of the imaging element array are formed at a wafer level,
wherein a lens array in a preceding row, a phase difference array, and a lens array in a subsequent row are defined as the optical elements, and
wherein the imaging device further includes a camera array configured with the optical elements and the imaging element array.

(32) The imaging device according to (31),
wherein the imaging element array includes at least one or more imaging element areas for capturing a unit image of a monochrome image or an image generated by an RGB color filter, which does not have a phase difference and is not an interference image.

(33) The imaging device according to (32),
wherein the imaging element area is 4n (n is an integer of 1 or greater) times the imaging area of the unit image for the hyper spectral imaging (HSI) data cube.

(34) The imaging device according to any one of (25) to (33),
wherein one set of polarizers of four orientations is arranged for respective four imaging areas in the phase difference array, with respect to the camera array, and
wherein the signal processing unit calculates a Stokes parameter or a Jones vector of each image point in the unit image, based on pixel signals of the imaging areas of the one set of polarizers.

(35) An imaging method of an imaging device, the imaging device including an imaging element array that captures a same imaging area, as a plurality of unit images, and a phase difference array that causes respective different optical path differences in a portion of respective imaging areas of the plurality of unit images which are captured by the imaging element array, the method causing
the imaging element array to capture the same imaging area, as the plurality of unit images, and
the phase difference array to cause the respective different optical path differences in a portion of respective imaging areas of the plurality of unit images which are captured by the imaging element array.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

11 Blood test apparatus
12 Arm
12a Artery
12b Vein
31 Body
32, 32-1, 32-2 Light source
33 Display unit
34 Belt
51 Camera array
52 Signal processing unit 71 Lens array
72 Phase difference array
72a Light shielding portion
72b Object
73 Lens array
74 Imaging element array

The invention claimed is:

1. An imaging device, comprising:
a phase difference array having a plurality of phase difference elements arranged along a plane and configured to provide different optical paths for light provided as a plurality of sets of light beams simultaneously transmitted through the phase difference array,
wherein the plurality of phase difference elements include a first phase difference element configured to generate a first optical path difference between a first portion of a first set of the plurality of sets of light beams incident on a first part of the first phase difference element and a second portion of the first set of light beams incident on a second part of the first phase difference element, and a second phase difference element configured to generate a second optical path difference between a first portion of a second set of the plurality of sets of light beams incident on a first part of the second phase difference element and a second portion of the second set of light beams incident on a second part of the first phase difference element, wherein the first phase difference element and the second phase difference element are arranged adjacent to each other along the plane; and
an imaging element array including a plurality of imaging elements,
wherein the plurality of imaging elements includes a first imaging element configured to receive the first set of light beams transmitted through the first phase difference element of the phase difference array and a second imaging element configured to receive the second set of light beams transmitted through the second phase difference element of the phase difference array.

2. The imaging device of claim 1, further comprising:
an objective lens array, wherein the objective lens array includes a plurality of objective lenses, and wherein the objective lens array is configured to provide the plurality of sets of light beams to the phase difference array.

3. The imaging device of claim 2, wherein the plurality of sets of light beams provided by the objective lens array are cylindrical parallel light beams.

4. The imaging device of claim 1, wherein for the first phase difference and/or the second phase difference element, a thickness of the first part of the phase difference element is different than a thickness of the second part of the phase difference element.

5. The imaging device of claim 4, wherein the first part of the phase difference element has a semicircular area.

6. The imaging device of claim 4, wherein the first part of the phase difference element has a cylindrical area.

7. The imaging device of claim 4, wherein individual phase difference elements of the plurality of phase difference elements in the phase difference array have thicknesses of the first part that increase from a phase difference element at a first end of the phase difference array to a phase difference element at a second end of the phase difference array.

8. The imaging device of claim 1, further comprising: a polarizer array, wherein the polarizer array includes four different types of polarizers that differ from one another by at least 45 degrees.

9. The imaging device of claim 1, further comprising: an imaging lens array including a plurality of imaging lenses, wherein the imaging lens array is positioned between the phase difference array and the imaging element array.

10. The imaging device of claim 9, wherein the plurality of imaging lenses of the imaging lens array are configured to focus the plurality of sets of light beams transmitted through the phase difference array onto at least some of the imaging elements.

11. The imaging device of claim 1, wherein each of the plurality of imaging elements includes a plurality of pixels.

12. The imaging device of claim 1, wherein light from a first area of an imaged object is included in a first one of the plurality of sets of light beams, and wherein light from the first area of the imaged object is included in a second one of the plurality of sets of light beams.

13. The imaging device of claim 1, wherein the plurality of phase difference elements are arranged in a two-dimensional array.

14. A detection apparatus, comprising:
a connecting structure;
a light source, wherein the light source is connected to the connecting structure;
an enclosure, wherein the enclosure is connected to the connecting structure, and wherein the enclosure includes:
a phase difference array having a plurality of phase difference elements arranged along a plane and configured to provide different optical paths for light provided as a plurality of sets of light beams simultaneously transmitted through the phase difference array, wherein the plurality of phase difference elements include a first phase difference element configured to generate a first optical path difference between a first portion of a first set of the plurality of sets of light beams incident on a first part of the first phase difference element and a second portion of the first set of light beams incident on a second part of the first phase difference element, and a second phase difference element configured to generate a second optical path difference between a first portion of a second set of the plurality of sets of light beams incident on a first part of the second phase difference element and a second portion of the second set of light beams incident on a second part of the first phase difference element, wherein the first phase difference element and the second phase difference element are arranged adjacent to each other along the plane;
an imaging element array including a plurality of imaging elements, wherein the plurality of imaging elements includes a first imaging element configured to receive the first set of light beams transmitted through the first phase difference element of the phase difference array and a second imaging element configured to receive the second set of light beams transmitted through the second phase difference element of the phase difference array; and
a display, wherein the display is connected to the connecting structure, and wherein the display is operable to display detection information generated from data provided by the imaging element array.

15. The detection apparatus of claim 14, further comprising: an objective lens array, wherein the object lens array includes a plurality of objective lenses, and wherein the objective lens array is configured to provide the plurality of sets of light beams to the phase difference array.

16. The detection apparatus of claim 15, wherein the plurality of sets of light beams provided by the objective lens array are cylindrical parallel light beams.

17. The detection apparatus of claim 14, wherein for the first phase difference element and/or the second phase difference element, a thickness of the first part of the phase difference element is different than a thickness of the second part of the phase difference element.

18. The detection apparatus of claim 17, wherein the first part of the phase difference element has a semicircular area.

19. The detection apparatus of claim 17, wherein the first part of the phase difference element has a cylindrical area.

20. The detection apparatus of claim 17, wherein individual phase difference elements of the plurality of phase difference elements in the phase difference array have thicknesses of the first part that increase from a phase difference element at a first end of the phase difference array to a phase difference element at a second end of the phase difference array.

21. The detection apparatus of claim 14, wherein the enclosure further includes: a polarizer array, wherein the polarizer array includes four different types of polarizers that differ from one another by at least 45 degrees.

22. The detection apparatus of claim 14, wherein the connecting structure is a belt.

23. The detection apparatus of claim 14, wherein the plurality of phase difference elements are arranged in a two-dimensional array.

24. A method for detecting a physical property, comprising:
  emitting light onto an object;
  receiving light from the object at a plurality of phase difference elements included in a phase difference array, wherein the plurality of phase difference elements are arranged along a plane and configured to provide different optical paths for the received light simultaneously transmitted through the phase difference array, wherein the plurality of phase difference elements include a first phase difference element configured to generate a first optical path difference between a first portion of a light beam incident on a first part of the first phase difference element and a second portion of the light beam incident on a second part of the first phase difference element, and a second phase difference element configured to generate a second optical path difference between a first portion of a light beam incident on a first part of the second phase difference element and a second portion of the light beam incident on a second part of the first phase difference element, wherein the first phase difference element and the second phase difference element are arranged adjacent to each other along the plane;
  receiving light from the first and second phase difference elements at an imaging element array; and
  displaying information obtained from hyperspectral imaging (HIS) data based on output signals of the imaging element array.

* * * * *